(12) United States Patent
Hill

(10) Patent No.: US 9,051,388 B2
(45) Date of Patent: Jun. 9, 2015

(54) BROAD SPECTRUM ERBB LIGAND BINDING MOLECULES AND METHODS FOR PREPARING AND USING THEM

(75) Inventor: Jason Hill, Chicago, IL (US)

(73) Assignee: LIGACEPT LLC, Oak Brook, IL (US)

(*) Notice: Subject to any disclaimer, the term of this patent is extended or adjusted under 35 U.S.C. 154(b) by 0 days.

(21) Appl. No.: 13/359,755

(22) Filed: Jan. 27, 2012

(65) Prior Publication Data

US 2012/0263707 A1 Oct. 18, 2012

Related U.S. Application Data

(63) Continuation of application No. PCT/US2010/043533, filed on Jul. 28, 2010.

(60) Provisional application No. 61/286,265, filed on Dec. 14, 2009, provisional application No. 61/229,224, filed on Jul. 28, 2009.

(51) Int. Cl.
| | |
|---|---|
| *C07K 14/00* | (2006.01) |
| *C07K 14/475* | (2006.01) |
| *C07K 14/705* | (2006.01) |
| *C07K 14/71* | (2006.01) |
| *A61K 38/17* | (2006.01) |
| *A61K 38/00* | (2006.01) |

(52) U.S. Cl.
CPC ............. *C07K 14/475* (2013.01); *C07K 14/705* (2013.01); *C07K 14/71* (2013.01); *A61K 38/177* (2013.01); *A61K 38/179* (2013.01); *C07K 2319/32* (2013.01); *A61K 38/00* (2013.01); *C07K 2319/30* (2013.01)

(58) Field of Classification Search
CPC ...... C07K 14/47; C07K 14/705; C07K 14/71; C07K 19/00; C07K 2319/30; C07K 2319/32; A61K 38/17; A61K 38/1709; A61K 38/177; A61K 38/179
USPC .................. 530/402; 514/7.5, 7.6, 19.2, 19.3
See application file for complete search history.

(56) References Cited

FOREIGN PATENT DOCUMENTS

WO WO 2007092932 A2 * 8/2007

OTHER PUBLICATIONS

Kim, J.H., et al, Eur. J. Biochem., 2323-2329, 2002.*
Burgess, A.W., et al. Molecular Cell, 12: 541-552, 2003.*

* cited by examiner

*Primary Examiner* — Misook Yu
*Assistant Examiner* — Anne Holleran
(74) *Attorney, Agent, or Firm* — Robert M. Gould; Husch Blackwell LLP

(57) ABSTRACT

Chimeric ErbB ligand binding molecules having detectable binding activity for more ErbB ligands than any one of native ErbB 1, ErbB3 or ErbB4 are disclosed. Preferably, the binding molecules bind a broad spectrum and, more preferably, the full spectrum of ErbB ligands. The chimeric ErbB ligand binding molecules generally have a subunit LI derived from one of ErbB1, 3, or 4 and a subunit LII derived from another distinct ErbB receptor type. The sub-domain, SI, which joins LI and LII can be from either one of the receptor types or can have portions from both. Pharmaceutical compositions that contain the molecules and methods for the treatment of ErbB sensitive diseases are also disclosed.

3 Claims, 5 Drawing Sheets

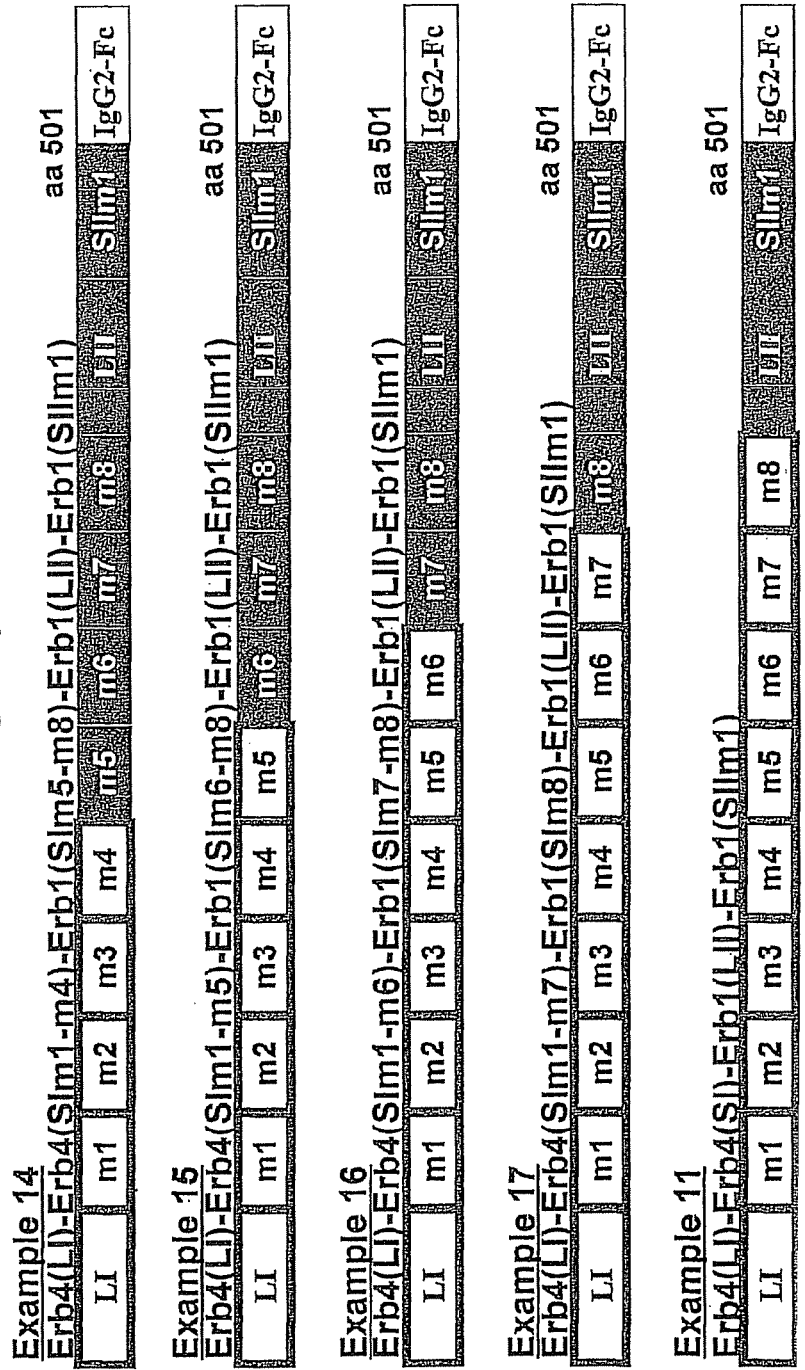

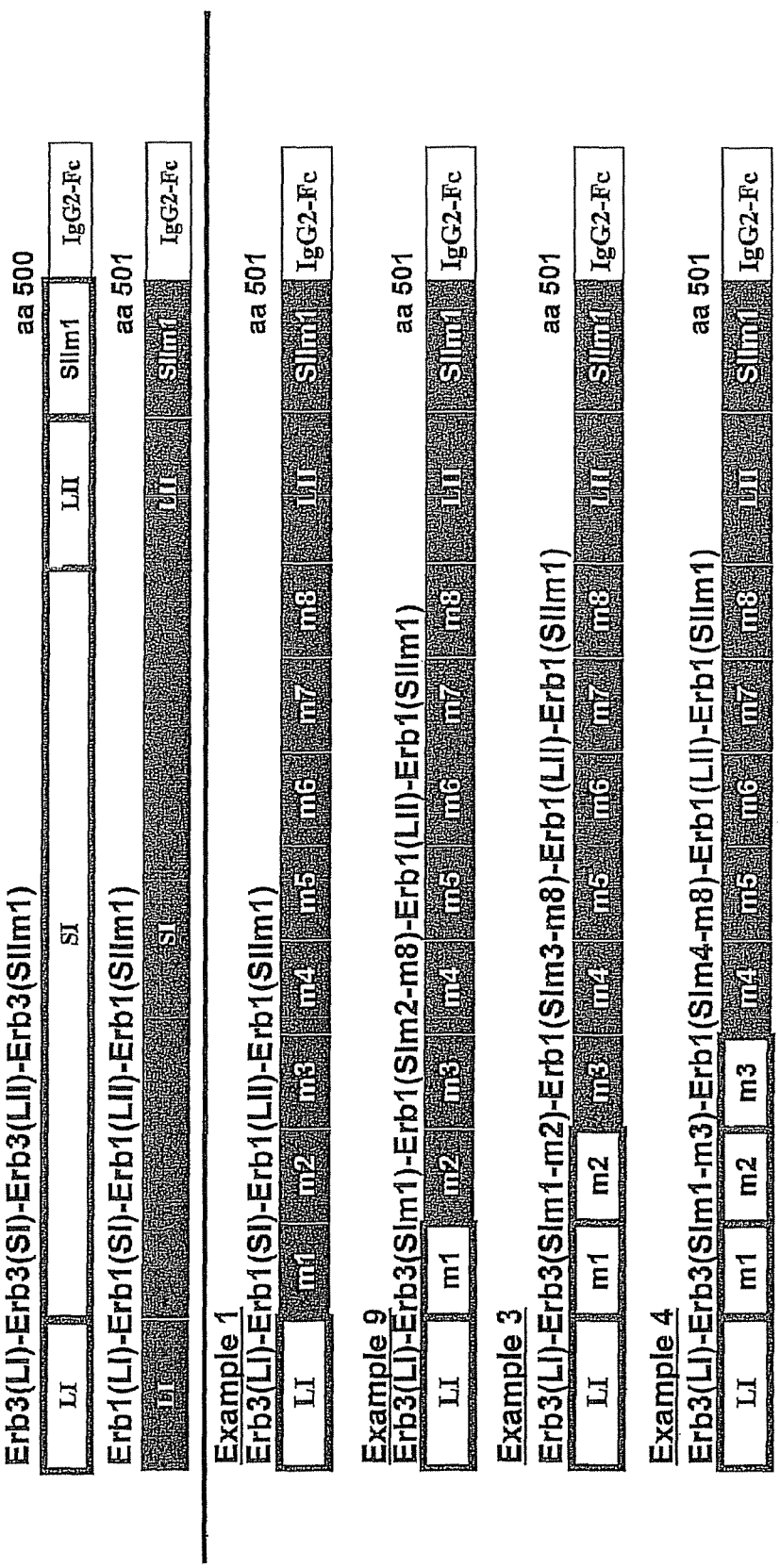

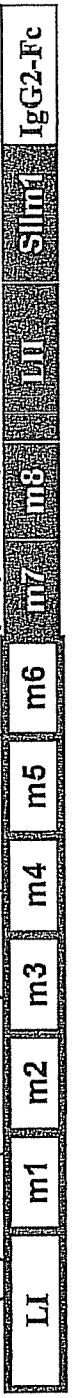
FIGURE 2 (CONTINUED)
Chimeric ErbB3 – ErbB1 designs (domains not drawn to scale)

FIGURE 3

| | |
|---|---|
| ErbB4_ECD | ---QSVCAGTENKLSSLSDLEQQYRALRKYYENCEVVMGNLEITSIEHNRDLSFLRSVRE |
| ErbB1_ECD | LEEKKVCQGTSNKLTQLGTFEDHFLSLQRMFNNCEVVLGNLEITYVQRNYDLSFLKTIQE |
| | |
| ErbB4_ECD | VTGYVLVALNQFRYLPLENLRIIRGTKLYEDRYALAIFLNYRKDGNFGLQELGLKNLTEI |
| ErbB1_ECD | VAGYVLIALNTVERIPLENLQIIRGNMYYENSYALAVLSNYDAN-KTGLKELPMRNLQEI |
| | |
| ErbB4_ECD | LNGGVYVDQNKFLCYADTIHWQDIVRNPWPSNLTLVSTNGSSGCGRCHKSCT-GRCWGPT |
| ErbB1_ECD | LHGAVRFSNNPALCNVESIQWRDIVSSDFLSNMSMDFQNHLGSCQKCDPSCPNGSCWGAG |
| | |
| ErbB4_ECD | ENHCQTLTRTVCAEQCDGRCYGPYVSDCCHRECAGGCSGPKDTDCFACMNFNDSGACVTQ |
| ErbB1_ECD | EENCQKLTKIICAQQCSGRCRGKSPSDCCHNQCAAGCTGPRESDCLVCRKFRDEATCKDT |
| | |
| ErbB4_ECD | CPQTFVYNPTTFQLEHNFNAKYTYGAFCVKKCPHNFVVDSS-SCVRACPSSKMEVEENGI |
| ErbB1_ECD | CPPLMLYNPTTYQMDVNPEGKYSFGATCVKKCPRNYVVTDHGSCVRACGADSYEMEEDGV |
| | |
| ErbB4_ECD | KMCKPCTDICPKACDGIGTGSLMSAQTVDSSNIDKFINCTKINGNLIFLVTGIHGDPYNA |
| ErbB1_ECD | RKCKKCEGPCRKVCNGIGIGEFKDSLSINATNIKHFKNCTSISGDLHILPVAFRGDSFTH |
| | |
| ErbB4_ECD | IEAIDPEKLNVFRTVREITGFLNIQSWPPNMTDFSVFSNLVTIGGRVLYSGLSLLILKQQ |
| ErbB1_ECD | TPPLDPQELDILKTVKEITGFLLIQAWPENRTDLHAFENLEIIRGRTKQHGQFSLAVVSL |
| | |
| ErbB4_ECD | GITSLQFQSLKEISAGNIYITDNSNLCYYHTINWTTLFSTINQRIVIRDNRKAENCTAEG |
| ErbB1_ECD | NITSLGLRSLKEISDGDVIISGNKNLCYANTINWKKLFGTSGQKTKIISNRGENSCKATG |
| | |
| ErbB4_ECD | MVCNHLCSSDGCWGPGPDQCLSCRRFSRGRICIESCNLYDGEFREFENGSICVECDPQCE |
| ErbB1_ECD | QVCHALCSPEGCWGPEPRDCVSCRNVSRGRECVDKCNLLEGEPREFVENSECIQCHPECL |
| | |
| ErbB4_ECD | KMEDGLLTCHGPGPDNCTKCSHFKDGPNCVEKCPDGLQGAN-SFIFKYADPDRECHPCHP |
| ErbB1_ECD | PQAMN-ITCTGRGPDNCIQCAHYIDGPHCVKTCPAGVMGENNTLVWKYADAGHVCHLCHP |
| | |
| ErbB4_ECD | NCTQGCNGPTSHDCIYYPWTGHSTLPQHARTP |
| ErbB1_ECD | NCTYGCTGPGLEGCP----TNGPKIPS----- |

SEQUENCE LISTING

<160> NUMBER OF SEQ ID NOS: 24

<210> SEQ ID NO 1
<211> LENGTH: 744
<212> TYPE: PRT
<213> ORGANISM: Artificial Sequence
<220> FEATURE:
<223> OTHER INFORMATION: Hybrid sequence derived from Homo sapien genes

<400> SEQUENCE: 1

Met Glu Trp Ser Trp Val Phe Leu Phe Phe Leu Ser Val Thr Thr Gly
1 5 10 15

Val His Ser Ser Glu Val Gly Asn Ser Gln Ala Val Cys Pro Gly Thr
20 25 30

Leu Asn Gly Leu Ser Val Thr Gly Asp Ala Glu Asn Gln Tyr Gln Thr
35 40 45

Leu Tyr Lys Leu Tyr Glu Arg Cys Glu Val Val Met Gly Asn Leu Glu
50 55 60

Ile Val Leu Thr Gly His Asn Ala Asp Leu Ser Phe Leu Gln Trp Ile
65 70 75 80

Arg Glu Val Thr Gly Tyr Val Leu Val Ala Met Asn Glu Phe Ser Thr
85 90 95

Leu Pro Leu Pro Asn Leu Arg Val Val Arg Gly Thr Gln Val Tyr Asp
100 105 110

Gly Lys Phe Ala Ile Phe Val Met Leu Asn Tyr Asn Thr Asn Ser Ser
115 120 125

His Ala Leu Arg Gln Leu Arg Leu Thr Gln Leu Thr Glu Ile Leu Ser
130 135 140

Gly Gly Val Tyr Ile Glu Lys Asn Asp Lys Leu Cys His Met Asp Thr
145 150 155 160

-continued

```
Ile Asp Trp Arg Asp Ile Val Arg Asp Arg Asp Ala Glu Ile Val Val
            165                 170                 175
Lys Asp Asn Gly Arg Ser Cys Pro Pro Cys Asp Pro Ser Cys Pro Asn
        180                 185                 190
Gly Ser Cys Trp Gly Ala Gly Glu Glu Asn Cys Gln Lys Leu Thr Lys
    195                 200                 205
Ile Ile Cys Ala Gln Gln Cys Ser Gly Arg Cys Arg Gly Lys Ser Pro
210                 215                 220
Ser Asp Cys Cys His Asn Gln Cys Ala Ala Gly Cys Thr Gly Pro Arg
225                 230                 235                 240
Glu Ser Asp Cys Leu Val Cys Arg Lys Phe Arg Asp Glu Ala Thr Cys
                245                 250                 255
Lys Asp Thr Cys Pro Pro Leu Met Leu Tyr Asn Pro Thr Thr Tyr Gln
            260                 265                 270
Met Asp Val Asn Pro Glu Gly Lys Tyr Ser Phe Gly Ala Thr Cys Val
        275                 280                 285
Lys Lys Cys Pro Arg Asn Tyr Val Val Thr Asp His Gly Ser Cys Val
    290                 295                 300
Arg Ala Cys Gly Ala Asp Ser Tyr Glu Met Glu Glu Asp Gly Val Arg
305                 310                 315                 320
Lys Cys Lys Lys Cys Glu Gly Pro Cys Arg Lys Val Cys Asn Gly Ile
                325                 330                 335
Gly Ile Gly Glu Phe Lys Asp Ser Leu Ser Ile Asn Ala Thr Asn Ile
            340                 345                 350
Lys His Phe Lys Asn Cys Thr Ser Ile Ser Gly Asp Leu His Ile Leu
        355                 360                 365
Pro Val Ala Phe Arg Gly Asp Ser Phe Thr His Thr Pro Pro Leu Asp
    370                 375                 380
Pro Gln Glu Leu Asp Ile Leu Lys Thr Val Lys Glu Ile Thr Gly Phe
385                 390                 395                 400
Leu Leu Ile Gln Ala Trp Pro Glu Asn Arg Thr Asp Leu His Ala Phe
                405                 410                 415
Glu Asn Leu Glu Ile Ile Arg Gly Arg Thr Lys Gln His Gly Gln Phe
            420                 425                 430
Ser Leu Ala Val Val Ser Leu Asn Ile Thr Ser Leu Gly Leu Arg Ser
        435                 440                 445
Leu Lys Glu Ile Ser Asp Gly Asp Val Ile Ile Ser Gly Asn Lys Asn
    450                 455                 460
Leu Cys Tyr Ala Asn Thr Ile Asn Trp Lys Lys Leu Phe Gly Thr Ser
465                 470                 475                 480
Gly Gln Lys Thr Lys Ile Ile Ser Asn Arg Gly Glu Asn Ser Cys Lys
                485                 490                 495
Ala Thr Gly Gln Val Cys His Ala Leu Cys Ser Pro Glu Gly Cys Trp
            500                 505                 510
Gly Pro Glu Pro Arg Asp Cys Val Ser Val Glu Cys Pro Pro Cys Pro
        515                 520                 525
Ala Pro Pro Val Ala Gly Pro Ser Val Phe Leu Phe Pro Pro Lys Pro
    530                 535                 540
Lys Asp Thr Leu Met Ile Ser Arg Thr Pro Glu Val Thr Cys Val Val
545                 550                 555                 560
Val Asp Val Ser His Glu Asp Pro Glu Val Gln Phe Asn Trp Tyr Val
                565                 570                 575
Asp Gly Met Glu Val His Asn Ala Lys Thr Lys Pro Arg Glu Glu Gln
```

```
                    580                 585                 590
Phe Asn Ser Thr Phe Arg Val Val Ser Val Leu Thr Val Val His Gln
            595                 600                 605

Asp Trp Leu Asn Gly Lys Glu Tyr Lys Cys Lys Val Ser Asn Lys Gly
        610                 615                 620

Leu Pro Ala Pro Ile Glu Lys Thr Ile Ser Lys Thr Lys Gly Gln Pro
625                 630                 635                 640

Arg Glu Pro Gln Val Tyr Thr Leu Pro Pro Ser Arg Glu Glu Met Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685

Lys Thr Thr Pro Pro Met Leu Asp Ser Asp Gly Ser Phe Phe Leu Tyr
690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740

<210> SEQ ID NO 2
<211> LENGTH: 742
<212> TYPE: PRT
<213> ORGANISM: Artificial Sequence
<220> FEATURE:
<223> OTHER INFORMATION: Hybrid sequence derived from Homo sapien genes

<400> SEQUENCE: 2

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
```

-continued

```
                195                 200                 205
Ile Cys Ala Pro Gln Cys Asn Gly His Cys Phe Gly Pro Asn Pro Asn
210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Val Cys Asn Gly Ile Gly Ile
                325                 330                 335
Gly Glu Phe Lys Asp Ser Leu Ser Ile Asn Ala Thr Asn Ile Lys His
            340                 345                 350
Phe Lys Asn Cys Thr Ser Ile Ser Gly Asp Leu His Ile Leu Pro Val
        355                 360                 365
Ala Phe Arg Gly Asp Ser Phe Thr His Thr Pro Pro Leu Asp Pro Gln
    370                 375                 380
Glu Leu Asp Ile Leu Lys Thr Val Lys Glu Ile Thr Gly Phe Leu Leu
385                 390                 395                 400
Ile Gln Ala Trp Pro Glu Asn Arg Thr Asp Leu His Ala Phe Glu Asn
                405                 410                 415
Leu Glu Ile Ile Arg Gly Arg Thr Lys Gln His Gly Gln Phe Ser Leu
            420                 425                 430
Ala Val Val Ser Leu Asn Ile Thr Ser Leu Gly Leu Arg Ser Leu Lys
        435                 440                 445
Glu Ile Ser Asp Gly Asp Val Ile Ile Ser Gly Asn Lys Asn Leu Cys
    450                 455                 460
Tyr Ala Asn Thr Ile Asn Trp Lys Lys Leu Phe Gly Thr Ser Gly Gln
465                 470                 475                 480
Lys Thr Lys Ile Ile Ser Asn Arg Gly Glu Asn Ser Cys Lys Ala Thr
                485                 490                 495
Gly Gln Val Cys His Ala Leu Cys Ser Pro Glu Gly Cys Trp Gly Pro
            500                 505                 510
Glu Pro Arg Asp Cys Val Ser Val Glu Cys Pro Pro Cys Pro Ala Pro
        515                 520                 525
Pro Val Ala Gly Pro Ser Val Phe Leu Phe Pro Pro Lys Pro Lys Asp
    530                 535                 540
Thr Leu Met Ile Ser Arg Thr Pro Glu Val Thr Cys Val Val Val Asp
545                 550                 555                 560
Val Ser His Glu Asp Pro Glu Val Gln Phe Asn Trp Tyr Val Asp Gly
                565                 570                 575
Met Glu Val His Asn Ala Lys Thr Lys Pro Arg Glu Glu Gln Phe Asn
            580                 585                 590
Ser Thr Phe Arg Val Val Ser Val Leu Thr Val Val His Gln Asp Trp
        595                 600                 605
Leu Asn Gly Lys Glu Tyr Lys Cys Lys Val Ser Asn Lys Gly Leu Pro
    610                 615                 620
```

```
Ala Pro Ile Glu Lys Thr Ile Ser Lys Thr Lys Gly Gln Pro Arg Glu
625                 630                 635                 640

Pro Gln Val Tyr Thr Leu Pro Pro Ser Arg Glu Glu Met Thr Lys Asn
            645                 650                 655

Gln Val Ser Leu Thr Cys Leu Val Lys Gly Phe Tyr Pro Ser Asp Ile
            660                 665                 670

Ala Val Glu Trp Glu Ser Asn Gly Gln Pro Glu Asn Asn Tyr Lys Thr
            675                 680                 685

Thr Pro Pro Met Leu Asp Ser Asp Gly Ser Phe Phe Leu Tyr Ser Lys
            690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly Lys
            740

<210> SEQ ID NO 3
<211> LENGTH: 743
<212> TYPE: PRT
<213> ORGANISM: Artificial Sequence
<220> FEATURE:
<223> OTHER INFORMATION: Hybrid sequence derived from Homo sapien genes

<400> SEQUENCE: 3

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asn Gln Cys Ala Ala Gly Cys Thr Gly Pro Arg Glu
225                 230                 235                 240
```

-continued

```
Ser Asp Cys Leu Val Cys Arg Lys Phe Arg Asp Glu Ala Thr Cys Lys
            245                 250                 255

Asp Thr Cys Pro Pro Leu Met Leu Tyr Asn Pro Thr Thr Tyr Gln Met
        260                 265                 270

Asp Val Asn Pro Glu Gly Lys Tyr Ser Phe Gly Ala Thr Cys Val Lys
            275                 280                 285

Lys Cys Pro Arg Asn Tyr Val Val Thr Asp His Gly Ser Cys Val Arg
        290                 295                 300

Ala Cys Gly Ala Asp Ser Tyr Glu Met Glu Glu Asp Gly Val Arg Lys
305                 310                 315                 320

Cys Lys Lys Cys Glu Gly Pro Cys Arg Lys Val Cys Asn Gly Ile Gly
                325                 330                 335

Ile Gly Glu Phe Lys Asp Ser Leu Ser Ile Asn Ala Thr Asn Ile Lys
            340                 345                 350

His Phe Lys Asn Cys Thr Ser Ile Ser Gly Asp Leu His Ile Leu Pro
        355                 360                 365

Val Ala Phe Arg Gly Asp Ser Phe Thr His Thr Pro Pro Leu Asp Pro
    370                 375                 380

Gln Glu Leu Asp Ile Leu Lys Thr Val Lys Glu Ile Thr Gly Phe Leu
385                 390                 395                 400

Leu Ile Gln Ala Trp Pro Glu Asn Arg Thr Asp Leu His Ala Phe Glu
                405                 410                 415

Asn Leu Glu Ile Ile Arg Gly Arg Thr Lys Gln His Gly Gln Phe Ser
            420                 425                 430

Leu Ala Val Val Ser Leu Asn Ile Thr Ser Leu Gly Leu Arg Ser Leu
        435                 440                 445

Lys Glu Ile Ser Asp Gly Asp Val Ile Ile Ser Gly Asn Lys Asn Leu
    450                 455                 460

Cys Tyr Ala Asn Thr Ile Asn Trp Lys Lys Leu Phe Gly Thr Ser Gly
465                 470                 475                 480

Gln Lys Thr Lys Ile Ile Ser Asn Arg Gly Glu Asn Ser Cys Lys Ala
                485                 490                 495

Thr Gly Gln Val Cys His Ala Leu Cys Ser Pro Glu Gly Cys Trp Gly
            500                 505                 510

Pro Glu Pro Arg Asp Cys Val Ser Val Glu Cys Pro Pro Cys Pro Ala
        515                 520                 525

Pro Pro Val Ala Gly Pro Ser Val Phe Leu Phe Pro Pro Lys Pro Lys
    530                 535                 540

Asp Thr Leu Met Ile Ser Arg Thr Pro Glu Val Thr Cys Val Val Val
545                 550                 555                 560

Asp Val Ser His Glu Asp Pro Glu Val Gln Phe Asn Trp Tyr Val Asp
                565                 570                 575

Gly Met Glu Val His Asn Ala Lys Thr Lys Pro Arg Glu Glu Gln Phe
            580                 585                 590

Asn Ser Thr Phe Arg Val Val Ser Val Leu Thr Val Val His Gln Asp
        595                 600                 605

Trp Leu Asn Gly Lys Glu Tyr Lys Cys Lys Val Ser Asn Lys Gly Leu
    610                 615                 620

Pro Ala Pro Ile Glu Lys Thr Ile Ser Lys Thr Lys Gly Gln Pro Arg
625                 630                 635                 640

Glu Pro Gln Val Tyr Thr Leu Pro Pro Ser Arg Glu Glu Met Thr Lys
                645                 650                 655
```

-continued

```
Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Met Leu Asp Ser Asp Gly Ser Phe Phe Leu Tyr Ser
    690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 4
<211> LENGTH: 743
<212> TYPE: PRT
<213> ORGANISM: Artificial Sequence
<220> FEATURE:
<223> OTHER INFORMATION: Hybrid sequence derived from Homo sapien genes

<400> SEQUENCE: 4

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Val Cys Arg Lys Phe Arg Asp Glu Ala Thr Cys Lys
                245                 250                 255

Asp Thr Cys Pro Pro Leu Met Leu Tyr Asn Pro Thr Thr Tyr Gln Met
            260                 265                 270
```

```
Asp Val Asn Pro Glu Gly Lys Tyr Ser Phe Gly Ala Thr Cys Val Lys
            275                 280                 285

Lys Cys Pro Arg Asn Tyr Val Val Thr Asp His Gly Ser Cys Val Arg
290                 295                 300

Ala Cys Gly Ala Asp Ser Tyr Glu Met Glu Glu Asp Gly Val Arg Lys
305                 310                 315                 320

Cys Lys Lys Cys Glu Gly Pro Cys Arg Lys Val Cys Asn Gly Ile Gly
                325                 330                 335

Ile Gly Glu Phe Lys Asp Ser Leu Ser Ile Asn Ala Thr Asn Ile Lys
            340                 345                 350

His Phe Lys Asn Cys Thr Ser Ile Ser Gly Asp Leu His Ile Leu Pro
        355                 360                 365

Val Ala Phe Arg Gly Asp Ser Phe Thr His Thr Pro Pro Leu Asp Pro
370                 375                 380

Gln Glu Leu Asp Ile Leu Lys Thr Val Lys Glu Ile Thr Gly Phe Leu
385                 390                 395                 400

Leu Ile Gln Ala Trp Pro Glu Asn Arg Thr Asp Leu His Ala Phe Glu
                405                 410                 415

Asn Leu Glu Ile Ile Arg Gly Arg Thr Lys Gln His Gly Gln Phe Ser
            420                 425                 430

Leu Ala Val Val Ser Leu Asn Ile Thr Ser Leu Gly Leu Arg Ser Leu
        435                 440                 445

Lys Glu Ile Ser Asp Gly Asp Val Ile Ile Ser Gly Asn Lys Asn Leu
    450                 455                 460

Cys Tyr Ala Asn Thr Ile Asn Trp Lys Lys Leu Phe Gly Thr Ser Gly
465                 470                 475                 480

Gln Lys Thr Lys Ile Ile Ser Asn Arg Gly Glu Asn Ser Cys Lys Ala
                485                 490                 495

Thr Gly Gln Val Cys His Ala Leu Cys Ser Pro Glu Gly Cys Trp Gly
            500                 505                 510

Pro Glu Pro Arg Asp Cys Val Ser Val Glu Cys Pro Pro Cys Pro Ala
        515                 520                 525

Pro Pro Val Ala Gly Pro Ser Val Phe Leu Phe Pro Pro Lys Pro Lys
530                 535                 540

Asp Thr Leu Met Ile Ser Arg Thr Pro Glu Val Thr Cys Val Val Val
545                 550                 555                 560

Asp Val Ser His Glu Asp Pro Glu Val Gln Phe Asn Trp Tyr Val Asp
                565                 570                 575

Gly Met Glu Val His Asn Ala Lys Thr Lys Pro Arg Glu Glu Gln Phe
            580                 585                 590

Asn Ser Thr Phe Arg Val Val Ser Val Leu Thr Val Val His Gln Asp
        595                 600                 605

Trp Leu Asn Gly Lys Glu Tyr Lys Cys Lys Val Ser Asn Lys Gly Leu
610                 615                 620

Pro Ala Pro Ile Glu Lys Thr Ile Ser Lys Thr Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Met Leu Asp Ser Asp Gly Ser Phe Phe Leu Tyr Ser
```

```
            690                 695                 700
Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 5
<211> LENGTH: 743
<212> TYPE: PRT
<213> ORGANISM: Artificial Sequence
<220> FEATURE:
<223> OTHER INFORMATION: Hybrid sequence derived from Homo sapien genes

<400> SEQUENCE: 5

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Thr Cys Pro Pro Leu Met Leu Tyr Asn Pro Thr Thr Tyr Gln Met
            260                 265                 270

Asp Val Asn Pro Glu Gly Lys Tyr Ser Phe Gly Ala Thr Cys Val Lys
        275                 280                 285

Lys Cys Pro Arg Asn Tyr Val Val Thr Asp His Gly Ser Cys Val Arg
    290                 295                 300

Ala Cys Gly Ala Asp Ser Tyr Glu Met Glu Glu Asp Gly Val Arg Lys
```

-continued

```
           305                 310                 315                 320
Cys Lys Lys Cys Glu Gly Pro Cys Arg Lys Val Cys Asn Gly Ile Gly
                325                 330                 335

Ile Gly Glu Phe Lys Asp Ser Leu Ser Ile Asn Ala Thr Asn Ile Lys
                340                 345                 350

His Phe Lys Asn Cys Thr Ser Ile Ser Gly Asp Leu His Ile Leu Pro
                355                 360                 365

Val Ala Phe Arg Gly Asp Ser Phe Thr His Thr Pro Pro Leu Asp Pro
370                 375                 380

Gln Glu Leu Asp Ile Leu Lys Thr Val Lys Glu Ile Thr Gly Phe Leu
385                 390                 395                 400

Leu Ile Gln Ala Trp Pro Glu Asn Arg Thr Asp Leu His Ala Phe Glu
                405                 410                 415

Asn Leu Glu Ile Ile Arg Gly Arg Thr Lys Gln His Gly Gln Phe Ser
                420                 425                 430

Leu Ala Val Val Ser Leu Asn Ile Thr Ser Leu Gly Leu Arg Ser Leu
                435                 440                 445

Lys Glu Ile Ser Asp Gly Asp Val Ile Ile Ser Gly Asn Lys Asn Leu
450                 455                 460

Cys Tyr Ala Asn Thr Ile Asn Trp Lys Lys Leu Phe Gly Thr Ser Gly
465                 470                 475                 480

Gln Lys Thr Lys Ile Ile Ser Asn Arg Gly Glu Asn Ser Cys Lys Ala
                485                 490                 495

Thr Gly Gln Val Cys His Ala Leu Cys Ser Pro Glu Gly Cys Trp Gly
                500                 505                 510

Pro Glu Pro Arg Asp Cys Val Ser Val Glu Cys Pro Pro Cys Pro Ala
515                 520                 525

Pro Pro Val Ala Gly Pro Ser Val Phe Leu Phe Pro Pro Lys Pro Lys
                530                 535                 540

Asp Thr Leu Met Ile Ser Arg Thr Pro Glu Val Thr Cys Val Val Val
545                 550                 555                 560

Asp Val Ser His Glu Asp Pro Glu Val Gln Phe Asn Trp Tyr Val Asp
                565                 570                 575

Gly Met Glu Val His Asn Ala Lys Thr Lys Pro Arg Glu Glu Gln Phe
                580                 585                 590

Asn Ser Thr Phe Arg Val Val Ser Val Leu Thr Val Val His Gln Asp
                595                 600                 605

Trp Leu Asn Gly Lys Glu Tyr Lys Cys Lys Val Ser Asn Lys Gly Leu
                610                 615                 620

Pro Ala Pro Ile Glu Lys Thr Ile Ser Lys Thr Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
                660                 665                 670

Ile Ala Val Glu Trp Glu Ser Asn Gly Gln Pro Glu Asn Asn Tyr Lys
                675                 680                 685

Thr Thr Pro Pro Met Leu Asp Ser Asp Gly Ser Phe Phe Leu Tyr Ser
                690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735
```

Leu Ser Leu Ser Pro Gly Lys
            740

<210> SEQ ID NO 6
<211> LENGTH: 743
<212> TYPE: PRT
<213> ORGANISM: Artificial Sequence
<220> FEATURE:
<223> OTHER INFORMATION: Hybrid sequence derived from Homo sapien genes

<400> SEQUENCE: 6

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Lys Cys Pro Arg Asn Tyr Val Val Thr Asp His Gly Ser Cys Val Arg
    290                 295                 300

Ala Cys Gly Ala Asp Ser Tyr Glu Met Glu Glu Asp Gly Val Arg Lys
305                 310                 315                 320

Cys Lys Lys Cys Glu Gly Pro Cys Arg Lys Val Cys Asn Gly Ile Gly
                325                 330                 335

Ile Gly Glu Phe Lys Asp Ser Leu Ser Ile Asn Ala Thr Asn Ile Lys
            340                 345                 350

His Phe Lys Asn Cys Thr Ser Ile Ser Gly Asp Leu His Ile Leu Pro
    355                 360                 365

Val Ala Phe Arg Gly Asp Ser Phe Thr His Thr Pro Pro Leu Asp Pro
    370                 375                 380

Gln Glu Leu Asp Ile Leu Lys Thr Val Lys Glu Ile Thr Gly Phe Leu
385                 390                 395                 400

Leu Ile Gln Ala Trp Pro Glu Asn Arg Thr Asp Leu His Ala Phe Glu
                405                 410                 415

Asn Leu Glu Ile Ile Arg Gly Arg Thr Lys Gln His Gly Gln Phe Ser
                420                 425                 430

Leu Ala Val Val Ser Leu Asn Ile Thr Ser Leu Gly Leu Arg Ser Leu
            435                 440                 445

Lys Glu Ile Ser Asp Gly Asp Val Ile Ile Ser Gly Asn Lys Asn Leu
    450                 455                 460

Cys Tyr Ala Asn Thr Ile Asn Trp Lys Lys Leu Phe Gly Thr Ser Gly
465                 470                 475                 480

Gln Lys Thr Lys Ile Ile Ser Asn Arg Gly Glu Asn Ser Cys Lys Ala
                485                 490                 495

Thr Gly Gln Val Cys His Ala Leu Cys Ser Pro Glu Gly Cys Trp Gly
            500                 505                 510

Pro Glu Pro Arg Asp Cys Val Ser Val Glu Cys Pro Pro Cys Pro Ala
    515                 520                 525

Pro Pro Val Ala Gly Pro Ser Val Phe Leu Phe Pro Pro Lys Pro Lys
    530                 535                 540

Asp Thr Leu Met Ile Ser Arg Thr Pro Glu Val Thr Cys Val Val Val
545                 550                 555                 560

Asp Val Ser His Glu Asp Pro Glu Val Gln Phe Asn Trp Tyr Val Asp
                565                 570                 575

Gly Met Glu Val His Asn Ala Lys Thr Lys Pro Arg Glu Glu Gln Phe
            580                 585                 590

Asn Ser Thr Phe Arg Val Val Ser Val Leu Thr Val Val His Gln Asp
        595                 600                 605

Trp Leu Asn Gly Lys Glu Tyr Lys Cys Lys Val Ser Asn Lys Gly Leu
    610                 615                 620

Pro Ala Pro Ile Glu Lys Thr Ile Ser Lys Thr Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Met Leu Asp Ser Asp Gly Ser Phe Phe Leu Tyr Ser
    690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 7
<211> LENGTH: 742

```
<212> TYPE: PRT
<213> ORGANISM: Artificial Sequence
<220> FEATURE:
<223> OTHER INFORMATION: Hybrid sequence derived from Homo sapien genes

<400> SEQUENCE: 7

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
290                 295                 300

Cys Gly Ala Asp Ser Tyr Glu Met Glu Glu Asp Gly Val Arg Lys Cys
305                 310                 315                 320

Lys Lys Cys Glu Gly Pro Cys Arg Lys Val Cys Asn Gly Ile Gly Ile
                325                 330                 335

Gly Glu Phe Lys Asp Ser Leu Ser Ile Asn Ala Thr Asn Ile Lys His
            340                 345                 350

Phe Lys Asn Cys Thr Ser Ile Ser Gly Asp Leu His Ile Leu Pro Val
        355                 360                 365

Ala Phe Arg Gly Asp Ser Phe Thr His Thr Pro Pro Leu Asp Pro Gln
370                 375                 380
```

```
Glu Leu Asp Ile Leu Lys Thr Val Lys Glu Ile Thr Gly Phe Leu Leu
385                 390                 395                 400

Ile Gln Ala Trp Pro Glu Asn Arg Thr Asp Leu His Ala Phe Glu Asn
            405                 410                 415

Leu Glu Ile Ile Arg Gly Arg Thr Lys Gln His Gly Gln Phe Ser Leu
        420                 425                 430

Ala Val Val Ser Leu Asn Ile Thr Ser Leu Gly Leu Arg Ser Leu Lys
    435                 440                 445

Glu Ile Ser Asp Gly Asp Val Ile Ser Gly Asn Lys Asn Leu Cys
450                 455                 460

Tyr Ala Asn Thr Ile Asn Trp Lys Lys Leu Phe Gly Thr Ser Gly Gln
465                 470                 475                 480

Lys Thr Lys Ile Ile Ser Asn Arg Gly Glu Asn Ser Cys Lys Ala Thr
                485                 490                 495

Gly Gln Val Cys His Ala Leu Cys Ser Pro Glu Gly Cys Trp Gly Pro
            500                 505                 510

Glu Pro Arg Asp Cys Val Ser Val Glu Cys Pro Pro Cys Pro Ala Pro
        515                 520                 525

Pro Val Ala Gly Pro Ser Val Phe Leu Phe Pro Pro Lys Pro Lys Asp
    530                 535                 540

Thr Leu Met Ile Ser Arg Thr Pro Glu Val Thr Cys Val Val Val Asp
545                 550                 555                 560

Val Ser His Glu Asp Pro Glu Val Gln Phe Asn Trp Tyr Val Asp Gly
                565                 570                 575

Met Glu Val His Asn Ala Lys Thr Lys Pro Arg Glu Glu Gln Phe Asn
            580                 585                 590

Ser Thr Phe Arg Val Val Ser Val Leu Thr Val Val His Gln Asp Trp
        595                 600                 605

Leu Asn Gly Lys Glu Tyr Lys Cys Lys Val Ser Asn Lys Gly Leu Pro
    610                 615                 620

Ala Pro Ile Glu Lys Thr Ile Ser Lys Thr Lys Gly Gln Pro Arg Glu
625                 630                 635                 640

Pro Gln Val Tyr Thr Leu Pro Pro Ser Arg Glu Glu Met Thr Lys Asn
                645                 650                 655

Gln Val Ser Leu Thr Cys Leu Val Lys Gly Phe Tyr Pro Ser Asp Ile
            660                 665                 670

Ala Val Glu Trp Glu Ser Asn Gly Gln Pro Glu Asn Asn Tyr Lys Thr
        675                 680                 685

Thr Pro Pro Met Leu Asp Ser Asp Gly Ser Phe Phe Leu Tyr Ser Lys
    690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
                725                 730                 735

Ser Leu Ser Pro Gly Lys
            740

<210> SEQ ID NO 8
<211> LENGTH: 742
<212> TYPE: PRT
<213> ORGANISM: Artificial Sequence
<220> FEATURE:
<223> OTHER INFORMATION: Hybrid sequence derived from Homo sapien genes

<400> SEQUENCE: 8
```

-continued

```
Met Glu Trp Ser Trp Val Phe Leu Phe Phe Leu Ser Val Thr Thr Gly
 1               5                  10                 15

Val His Ser Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Glu Gly Pro Cys Arg Lys Val Cys Asn Gly Ile Gly Ile
                325                 330                 335

Gly Glu Phe Lys Asp Ser Leu Ser Ile Asn Ala Thr Asn Ile Lys His
            340                 345                 350

Phe Lys Asn Cys Thr Ser Ile Ser Gly Asp Leu His Ile Leu Pro Val
            355                 360                 365

Ala Phe Arg Gly Asp Ser Phe Thr His Thr Pro Pro Leu Asp Pro Gln
            370                 375                 380

Glu Leu Asp Ile Leu Lys Thr Val Lys Glu Ile Thr Gly Phe Leu Leu
385                 390                 395                 400

Ile Gln Ala Trp Pro Glu Asn Arg Thr Asp Leu His Ala Phe Glu Asn
                405                 410                 415

Leu Glu Ile Ile Arg Gly Arg Thr Lys Gln His Gly Gln Phe Ser Leu
```

```
            420                 425                 430
Ala Val Val Ser Leu Asn Ile Thr Ser Leu Gly Leu Arg Ser Leu Lys
                435                 440                 445

Glu Ile Ser Asp Gly Asp Val Ile Ser Gly Asn Lys Asn Leu Cys
450                 455                 460

Tyr Ala Asn Thr Ile Asn Trp Lys Lys Leu Phe Gly Thr Ser Gly Gln
465                 470                 475                 480

Lys Thr Lys Ile Ile Ser Asn Arg Gly Glu Asn Ser Cys Lys Ala Thr
                485                 490                 495

Gly Gln Val Cys His Ala Leu Cys Ser Pro Glu Gly Cys Trp Gly Pro
                500                 505                 510

Glu Pro Arg Asp Cys Val Ser Val Glu Cys Pro Pro Cys Ala Pro
                515                 520                 525

Pro Val Ala Gly Pro Ser Val Phe Leu Phe Pro Pro Lys Pro Lys Asp
                530                 535                 540

Thr Leu Met Ile Ser Arg Thr Pro Glu Val Thr Cys Val Val Val Asp
545                 550                 555                 560

Val Ser His Glu Asp Pro Glu Val Gln Phe Asn Trp Tyr Val Asp Gly
                565                 570                 575

Met Glu Val His Asn Ala Lys Thr Lys Pro Arg Glu Glu Gln Phe Asn
                580                 585                 590

Ser Thr Phe Arg Val Val Ser Val Leu Thr Val Val His Gln Asp Trp
                595                 600                 605

Leu Asn Gly Lys Glu Tyr Lys Cys Lys Val Ser Asn Lys Gly Leu Pro
                610                 615                 620

Ala Pro Ile Glu Lys Thr Ile Ser Lys Thr Lys Gly Gln Pro Arg Glu
625                 630                 635                 640

Pro Gln Val Tyr Thr Leu Pro Pro Ser Arg Glu Glu Met Thr Lys Asn
                645                 650                 655

Gln Val Ser Leu Thr Cys Leu Val Lys Gly Phe Tyr Pro Ser Asp Ile
                660                 665                 670

Ala Val Glu Trp Glu Ser Asn Gly Gln Pro Glu Asn Asn Tyr Lys Thr
                675                 680                 685

Thr Pro Pro Met Leu Asp Ser Asp Gly Ser Phe Phe Leu Tyr Ser Lys
                690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
                725                 730                 735

Ser Leu Ser Pro Gly Lys
                740

<210> SEQ ID NO 9
<211> LENGTH: 743
<212> TYPE: PRT
<213> ORGANISM: Artificial Sequence
<220> FEATURE:
<223> OTHER INFORMATION: Hybrid sequence derived from Homo sapien genes

<400> SEQUENCE: 9

Met Glu Trp Ser Trp Val Phe Leu Phe Phe Leu Ser Val Thr Thr Gly
1               5                   10                  15

Val His Ser Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
```

```
            35                  40                  45
Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                     85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Ile
                195                 200                 205

Ile Cys Ala Gln Gln Cys Ser Gly Arg Cys Arg Gly Lys Ser Pro Ser
210                 215                 220

Asp Cys Cys His Asn Gln Cys Ala Ala Gly Cys Thr Gly Pro Arg Glu
225                 230                 235                 240

Ser Asp Cys Leu Val Cys Arg Lys Phe Arg Asp Glu Ala Thr Cys Lys
                245                 250                 255

Asp Thr Cys Pro Pro Leu Met Leu Tyr Asn Pro Thr Thr Tyr Gln Met
                260                 265                 270

Asp Val Asn Pro Glu Gly Lys Tyr Ser Phe Gly Ala Thr Cys Val Lys
                275                 280                 285

Lys Cys Pro Arg Asn Tyr Val Val Thr Asp His Gly Ser Cys Val Arg
            290                 295                 300

Ala Cys Gly Ala Asp Ser Tyr Glu Met Glu Glu Asp Gly Val Arg Lys
305                 310                 315                 320

Cys Lys Lys Cys Glu Gly Pro Cys Arg Lys Val Cys Asn Gly Ile Gly
                325                 330                 335

Ile Gly Glu Phe Lys Asp Ser Leu Ser Ile Asn Ala Thr Asn Ile Lys
                340                 345                 350

His Phe Lys Asn Cys Thr Ser Ile Ser Gly Asp Leu His Ile Leu Pro
            355                 360                 365

Val Ala Phe Arg Gly Asp Ser Phe Thr His Thr Pro Pro Leu Asp Pro
370                 375                 380

Gln Glu Leu Asp Ile Leu Lys Thr Val Lys Glu Ile Thr Gly Phe Leu
385                 390                 395                 400

Leu Ile Gln Ala Trp Pro Glu Asn Arg Thr Asp Leu His Ala Phe Glu
                405                 410                 415

Asn Leu Glu Ile Ile Arg Gly Arg Thr Lys Gln His Gly Gln Phe Ser
                420                 425                 430

Leu Ala Val Val Ser Leu Asn Ile Thr Ser Leu Gly Leu Arg Ser Leu
            435                 440                 445

Lys Glu Ile Ser Asp Gly Asp Val Ile Ile Ser Gly Asn Lys Asn Leu
450                 455                 460
```

```
Cys Tyr Ala Asn Thr Ile Asn Trp Lys Lys Leu Phe Gly Thr Ser Gly
465                 470                 475                 480

Gln Lys Thr Lys Ile Ile Ser Asn Arg Gly Glu Asn Ser Cys Lys Ala
            485                 490                 495

Thr Gly Gln Val Cys His Ala Leu Cys Ser Pro Glu Gly Cys Trp Gly
        500                 505                 510

Pro Glu Pro Arg Asp Cys Val Ser Val Glu Cys Pro Pro Cys Pro Ala
    515                 520                 525

Pro Pro Val Ala Gly Pro Ser Val Phe Leu Phe Pro Pro Lys Pro Lys
530                 535                 540

Asp Thr Leu Met Ile Ser Arg Thr Pro Glu Val Thr Cys Val Val Val
545                 550                 555                 560

Asp Val Ser His Glu Asp Pro Glu Val Gln Phe Asn Trp Tyr Val Asp
                565                 570                 575

Gly Met Glu Val His Asn Ala Lys Thr Lys Pro Arg Glu Glu Gln Phe
            580                 585                 590

Asn Ser Thr Phe Arg Val Val Ser Val Leu Thr Val His Gln Asp
        595                 600                 605

Trp Leu Asn Gly Lys Glu Tyr Lys Cys Lys Val Ser Asn Lys Gly Leu
    610                 615                 620

Pro Ala Pro Ile Glu Lys Thr Ile Ser Lys Thr Lys Gly Gln Pro Arg
625                 630                 635                 640

Glu Pro Gln Val Tyr Thr Leu Pro Pro Ser Arg Glu Glu Met Thr Lys
                645                 650                 655

Asn Gln Val Ser Leu Thr Cys Leu Val Lys Gly Phe Tyr Pro Ser Asp
            660                 665                 670

Ile Ala Val Glu Trp Glu Ser Asn Gly Gln Pro Glu Asn Asn Tyr Lys
        675                 680                 685

Thr Thr Pro Pro Met Leu Asp Ser Asp Gly Ser Phe Phe Leu Tyr Ser
690                 695                 700

Lys Leu Thr Val Asp Lys Ser Arg Trp Gln Gln Gly Asn Val Phe Ser
705                 710                 715                 720

Cys Ser Val Met His Glu Ala Leu His Asn His Tyr Thr Gln Lys Ser
                725                 730                 735

Leu Ser Leu Ser Pro Gly Lys
            740

<210> SEQ ID NO 10
<211> LENGTH: 741
<212> TYPE: PRT
<213> ORGANISM: Artificial Sequence
<220> FEATURE:
<223> OTHER INFORMATION: Hybrid sequence derived from Homo sapien genes

<400> SEQUENCE: 10

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80
```

```
Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
                100                 105                 110

Ile Phe Leu Asn Tyr Arg Lys Asp Gly Asn Phe Gly Leu Gln Glu Leu
                115                 120                 125

Gly Leu Lys Asn Leu Thr Glu Ile Leu Asn Gly Gly Val Tyr Val Asp
            130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys Asp Pro Ser Cys Pro Asn Gly Ser Cys
                180                 185                 190

Trp Gly Ala Gly Glu Glu Asn Cys Gln Lys Leu Thr Lys Ile Ile Cys
                195                 200                 205

Ala Gln Gln Cys Ser Gly Arg Cys Arg Gly Lys Ser Pro Ser Asp Cys
            210                 215                 220

Cys His Asn Gln Cys Ala Ala Gly Cys Thr Gly Pro Arg Glu Ser Asp
225                 230                 235                 240

Cys Leu Val Cys Arg Lys Phe Arg Asp Glu Ala Thr Cys Lys Asp Thr
                245                 250                 255

Cys Pro Pro Leu Met Leu Tyr Asn Pro Thr Thr Tyr Gln Met Asp Val
                260                 265                 270

Asn Pro Glu Gly Lys Tyr Ser Phe Gly Ala Thr Cys Val Lys Lys Cys
                275                 280                 285

Pro Arg Asn Tyr Val Val Thr Asp His Gly Ser Cys Val Arg Ala Cys
            290                 295                 300

Gly Ala Asp Ser Tyr Glu Met Glu Glu Asp Gly Val Arg Lys Cys Lys
305                 310                 315                 320

Lys Cys Glu Gly Pro Cys Arg Lys Val Cys Asn Gly Ile Gly Ile Gly
                325                 330                 335

Glu Phe Lys Asp Ser Leu Ser Ile Asn Ala Thr Asn Ile Lys His Phe
                340                 345                 350

Lys Asn Cys Thr Ser Ile Ser Gly Asp Leu His Ile Leu Pro Val Ala
                355                 360                 365

Phe Arg Gly Asp Ser Phe Thr His Thr Pro Pro Leu Asp Pro Gln Glu
            370                 375                 380

Leu Asp Ile Leu Lys Thr Val Lys Glu Ile Thr Gly Phe Leu Leu Ile
385                 390                 395                 400

Gln Ala Trp Pro Glu Asn Arg Thr Asp Leu His Ala Phe Glu Asn Leu
                405                 410                 415

Glu Ile Ile Arg Gly Arg Thr Lys Gln His Gly Gln Phe Ser Leu Ala
                420                 425                 430

Val Val Ser Leu Asn Ile Thr Ser Leu Gly Leu Arg Ser Leu Lys Glu
            435                 440                 445

Ile Ser Asp Gly Asp Val Ile Ile Ser Gly Asn Lys Asn Leu Cys Tyr
450                 455                 460

Ala Asn Thr Ile Asn Trp Lys Lys Leu Phe Gly Thr Ser Gly Gln Lys
465                 470                 475                 480

Thr Lys Ile Ile Ser Asn Arg Gly Glu Asn Ser Cys Lys Ala Thr Gly
                485                 490                 495
```

```
Gln Val Cys His Ala Leu Cys Ser Pro Gly Cys Trp Gly Pro Glu
            500                 505                 510

Pro Arg Asp Cys Val Ser Val Glu Cys Pro Pro Cys Pro Ala Pro Pro
        515                 520                 525

Val Ala Gly Pro Ser Val Phe Leu Phe Pro Pro Lys Pro Lys Asp Thr
    530                 535                 540

Leu Met Ile Ser Arg Thr Pro Glu Val Thr Cys Val Val Val Asp Val
545                 550                 555                 560

Ser His Glu Asp Pro Glu Val Gln Phe Asn Trp Tyr Val Asp Gly Met
            565                 570                 575

Glu Val His Asn Ala Lys Thr Lys Pro Arg Glu Glu Gln Phe Asn Ser
        580                 585                 590

Thr Phe Arg Val Val Ser Val Leu Thr Val Val His Gln Asp Trp Leu
    595                 600                 605

Asn Gly Lys Glu Tyr Lys Cys Lys Val Ser Asn Lys Gly Leu Pro Ala
610                 615                 620

Pro Ile Glu Lys Thr Ile Ser Lys Thr Lys Gly Gln Pro Arg Glu Pro
625                 630                 635                 640

Gln Val Tyr Thr Leu Pro Pro Ser Arg Glu Glu Met Thr Lys Asn Gln
            645                 650                 655

Val Ser Leu Thr Cys Leu Val Lys Gly Phe Tyr Pro Ser Asp Ile Ala
        660                 665                 670

Val Glu Trp Glu Ser Asn Gly Gln Pro Glu Asn Asn Tyr Lys Thr Thr
    675                 680                 685

Pro Pro Met Leu Asp Ser Asp Gly Ser Phe Phe Leu Tyr Ser Lys Leu
690                 695                 700

Thr Val Asp Lys Ser Arg Trp Gln Gln Gly Asn Val Phe Ser Cys Ser
705                 710                 715                 720

Val Met His Glu Ala Leu His Asn His Tyr Thr Gln Lys Ser Leu Ser
            725                 730                 735

Leu Ser Pro Gly Lys
            740

<210> SEQ ID NO 11
<211> LENGTH: 739
<212> TYPE: PRT
<213> ORGANISM: Artificial Sequence
<220> FEATURE:
<223> OTHER INFORMATION: Hybrid sequence derived from Homo sapien genes

<400> SEQUENCE: 11

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
            85                  90                  95

Arg Ile Ile Arg Gly Thr Lys Leu Tyr Glu Asp Arg Tyr Ala Leu Ala
            100                 105                 110
```

```
Ile Phe Leu Asn Tyr Arg Lys Asp Gly Asn Phe Gly Leu Gln Glu Leu
            115                 120                 125

Gly Leu Lys Asn Leu Thr Glu Ile Leu Asn Gly Val Tyr Val Asp
130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Arg Thr Val Cys Ala
            195                 200                 205

Glu Gln Cys Asp Gly Arg Cys Tyr Gly Pro Tyr Val Ser Asp Cys Cys
210                 215                 220

His Arg Glu Cys Ala Gly Gly Cys Ser Gly Pro Lys Asp Thr Asp Cys
225                 230                 235                 240

Phe Ala Cys Met Asn Phe Asn Asp Ser Gly Ala Cys Val Thr Gln Cys
                245                 250                 255

Pro Gln Thr Phe Val Tyr Asn Pro Thr Thr Phe Gln Leu Glu His Asn
            260                 265                 270

Phe Asn Ala Lys Tyr Thr Tyr Gly Ala Phe Cys Val Lys Lys Cys Pro
            275                 280                 285

His Asn Phe Val Val Asp Ser Ser Cys Val Arg Ala Cys Pro Ser
290                 295                 300

Ser Lys Met Glu Val Glu Glu Asn Gly Ile Lys Met Cys Lys Pro Cys
305                 310                 315                 320

Thr Asp Ile Cys Pro Lys Val Cys Asn Gly Ile Gly Ile Gly Glu Phe
                325                 330                 335

Lys Asp Ser Leu Ser Ile Asn Ala Thr Asn Ile Lys His Phe Lys Asn
            340                 345                 350

Cys Thr Ser Ile Ser Gly Asp Leu His Ile Leu Pro Val Ala Phe Arg
            355                 360                 365

Gly Asp Ser Phe Thr His Thr Pro Pro Leu Asp Pro Gln Glu Leu Asp
370                 375                 380

Ile Leu Lys Thr Val Lys Glu Ile Thr Gly Phe Leu Leu Ile Gln Ala
385                 390                 395                 400

Trp Pro Glu Asn Arg Thr Asp Leu His Ala Phe Glu Asn Leu Glu Ile
                405                 410                 415

Ile Arg Gly Arg Thr Lys Gln His Gly Gln Phe Ser Leu Ala Val Val
            420                 425                 430

Ser Leu Asn Ile Thr Ser Leu Gly Leu Arg Ser Leu Lys Glu Ile Ser
            435                 440                 445

Asp Gly Asp Val Ile Ile Ser Gly Asn Lys Asn Leu Cys Tyr Ala Asn
450                 455                 460

Thr Ile Asn Trp Lys Lys Leu Phe Gly Thr Ser Gly Gln Lys Thr Lys
465                 470                 475                 480

Ile Ile Ser Asn Arg Gly Glu Asn Ser Cys Lys Ala Thr Gly Gln Val
                485                 490                 495

Cys His Ala Leu Cys Ser Pro Glu Gly Cys Trp Gly Pro Glu Pro Arg
            500                 505                 510

Asp Cys Val Ser Val Glu Cys Pro Pro Cys Pro Ala Pro Pro Val Ala
            515                 520                 525

Gly Pro Ser Val Phe Leu Phe Pro Pro Lys Pro Lys Asp Thr Leu Met
```

```
                    530                 535                 540
Ile Ser Arg Thr Pro Glu Val Thr Cys Val Val Asp Val Ser His
545                 550                 555                 560

Glu Asp Pro Glu Val Gln Phe Asn Trp Tyr Val Asp Gly Met Glu Val
                565                 570                 575

His Asn Ala Lys Thr Lys Pro Arg Glu Glu Gln Phe Asn Ser Thr Phe
                580                 585                 590

Arg Val Val Ser Val Leu Thr Val His Gln Asp Trp Leu Asn Gly
                595                 600                 605

Lys Glu Tyr Lys Cys Lys Val Ser Asn Lys Gly Leu Pro Ala Pro Ile
                610                 615                 620

Glu Lys Thr Ile Ser Lys Thr Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
                660                 665                 670

Trp Glu Ser Asn Gly Gln Pro Glu Asn Asn Tyr Lys Thr Thr Pro Pro
                675                 680                 685

Met Leu Asp Ser Asp Gly Ser Phe Phe Leu Tyr Ser Lys Leu Thr Val
                690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
                725                 730                 735

Pro Gly Lys

<210> SEQ ID NO 12
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 12

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
                20                  25                  30

Leu Ser Asp Leu Glu Gln Gln Tyr Arg Ala Leu Arg Lys Tyr Tyr Glu
            35                  40                  45

Asn Cys Glu Val Val Met Gly Asn Leu Glu Ile Thr Ser Ile Glu His
50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
                100                 105                 110

Ile Phe Leu Asn Tyr Arg Lys Asp Gly Asn Phe Gly Leu Gln Glu Leu
            115                 120                 125

Gly Leu Lys Asn Leu Thr Glu Ile Leu Asn Gly Gly Val Tyr Val Asp
        130                 135                 140

Gln Asn Lys Phe Leu Cys Tyr Ala Asp Thr Ile His Trp Gln Asp Ile
145                 150                 155                 160
```

```
Val Arg Asn Pro Trp Pro Ser Asn Leu Thr Leu Val Ser Thr Asn Gly
            165                 170                 175

Ser Ser Gly Cys Gly Arg Cys His Lys Ser Cys Thr Gly Arg Cys Trp
        180                 185                 190

Gly Pro Thr Glu Asn His Cys Gln Thr Leu Thr Arg Thr Val Cys Ala
            195                 200                 205

Glu Gln Cys Asp Gly Arg Cys Tyr Gly Pro Tyr Val Ser Asp Cys Cys
    210                 215                 220

His Asn Gln Cys Ala Ala Gly Cys Thr Gly Pro Arg Glu Ser Asp Cys
225                 230                 235                 240

Leu Val Cys Arg Lys Phe Arg Asp Glu Ala Thr Cys Lys Asp Thr Cys
                245                 250                 255

Pro Pro Leu Met Leu Tyr Asn Pro Thr Thr Tyr Gln Met Asp Val Asn
            260                 265                 270

Pro Glu Gly Lys Tyr Ser Phe Gly Ala Thr Cys Val Lys Lys Cys Pro
        275                 280                 285

Arg Asn Tyr Val Val Thr Asp His Gly Ser Cys Val Arg Ala Cys Gly
        290                 295                 300

Ala Asp Ser Tyr Glu Met Glu Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
            340                 345                 350

Asn Cys Thr Ser Ile Ser Gly Asp Leu His Ile Leu Pro Val Ala Phe
        355                 360                 365

Arg Gly Asp Ser Phe Thr His Thr Pro Pro Leu Asp Pro Gln Glu Leu
        370                 375                 380

Asp Ile Leu Lys Thr Val Lys Glu Ile Thr Gly Phe Leu Leu Ile Gln
385                 390                 395                 400

Ala Trp Pro Glu Asn Arg Thr Asp Leu His Ala Phe Glu Asn Leu Glu
                405                 410                 415

Ile Ile Arg Gly Arg Thr Lys Gln His Gly Gln Phe Ser Leu Ala Val
            420                 425                 430

Val Ser Leu Asn Ile Thr Ser Leu Gly Leu Arg Ser Leu Lys Glu Ile
        435                 440                 445

Ser Asp Gly Asp Val Ile Ile Ser Gly Asn Lys Asn Leu Cys Tyr Ala
    450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
            500                 505                 510

Arg Asp Cys Val Ser Val Glu Cys Pro Pro Cys Pro Ala Pro Pro Val
        515                 520                 525

Ala Gly Pro Ser Val Phe Leu Phe Pro Pro Lys Pro Lys Asp Thr Leu
        530                 535                 540

Met Ile Ser Arg Thr Pro Glu Val Thr Cys Val Val Val Asp Val Ser
545                 550                 555                 560

His Glu Asp Pro Glu Val Gln Phe Asn Trp Tyr Val Asp Gly Met Glu
                565                 570                 575
```

```
Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
    610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 13
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 13

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190
```

-continued

```
Gly Pro Thr Glu Asn His Cys Gln Thr Leu Thr Arg Thr Val Cys Ala
            195                 200                 205
Glu Gln Cys Asp Gly Arg Cys Tyr Gly Pro Tyr Val Ser Asp Cys Cys
        210                 215                 220
His Arg Glu Cys Ala Gly Gly Cys Ser Gly Pro Lys Asp Thr Asp Cys
225                 230                 235                 240
Phe Val Cys Arg Lys Phe Arg Asp Glu Ala Thr Cys Lys Asp Thr Cys
                245                 250                 255
Pro Pro Leu Met Leu Tyr Asn Pro Thr Thr Tyr Gln Met Asp Val Asn
            260                 265                 270
Pro Glu Gly Lys Tyr Ser Phe Gly Ala Thr Cys Val Lys Lys Cys Pro
        275                 280                 285
Arg Asn Tyr Val Val Thr Asp His Gly Ser Cys Val Arg Ala Cys Gly
    290                 295                 300
Ala Asp Ser Tyr Glu Met Glu Glu Asp Gly Val Arg Lys Cys Lys Lys
305                 310                 315                 320
Cys Glu Gly Pro Cys Arg Lys Val Cys Asn Gly Ile Gly Ile Gly Glu
                325                 330                 335
Phe Lys Asp Ser Leu Ser Ile Asn Ala Thr Asn Ile Lys His Phe Lys
            340                 345                 350
Asn Cys Thr Ser Ile Ser Gly Asp Leu His Ile Leu Pro Val Ala Phe
        355                 360                 365
Arg Gly Asp Ser Phe Thr His Thr Pro Pro Leu Asp Pro Gln Glu Leu
    370                 375                 380
Asp Ile Leu Lys Thr Val Lys Glu Ile Thr Gly Phe Leu Leu Ile Gln
385                 390                 395                 400
Ala Trp Pro Glu Asn Arg Thr Asp Leu His Ala Phe Glu Asn Leu Glu
                405                 410                 415
Ile Ile Arg Gly Arg Thr Lys Gln His Gly Gln Phe Ser Leu Ala Val
            420                 425                 430
Val Ser Leu Asn Ile Thr Ser Leu Gly Leu Arg Ser Leu Lys Glu Ile
        435                 440                 445
Ser Asp Gly Asp Val Ile Ile Ser Gly Asn Lys Asn Leu Cys Tyr Ala
    450                 455                 460
Asn Thr Ile Asn Trp Lys Lys Leu Phe Gly Thr Ser Gly Gln Lys Thr
465                 470                 475                 480
Lys Ile Ile Ser Asn Arg Gly Glu Asn Ser Cys Lys Ala Thr Gly Gln
                485                 490                 495
Val Cys His Ala Leu Cys Ser Pro Glu Gly Cys Trp Gly Pro Glu Pro
            500                 505                 510
Arg Asp Cys Val Ser Val Glu Cys Pro Pro Cys Pro Ala Pro Pro Val
        515                 520                 525
Ala Gly Pro Ser Val Phe Leu Phe Pro Pro Lys Pro Lys Asp Thr Leu
    530                 535                 540
Met Ile Ser Arg Thr Pro Glu Val Thr Cys Val Val Val Asp Val Ser
545                 550                 555                 560
His Glu Asp Pro Glu Val Gln Phe Asn Trp Tyr Val Asp Gly Met Glu
                565                 570                 575
Val His Asn Ala Lys Thr Lys Pro Arg Glu Glu Gln Phe Asn Ser Thr
            580                 585                 590
Phe Arg Val Val Ser Val Leu Thr Val Val His Gln Asp Trp Leu Asn
        595                 600                 605
Gly Lys Glu Tyr Lys Cys Lys Val Ser Asn Lys Gly Leu Pro Ala Pro
```

```
            610                 615                 620
Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
                660                 665                 670

Glu Trp Glu Ser Asn Gly Gln Pro Glu Asn Asn Tyr Lys Thr Thr Pro
            675                 680                 685

Pro Met Leu Asp Ser Asp Gly Ser Phe Phe Leu Tyr Ser Lys Leu Thr
        690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 14
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 14

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
                20                  25                  30

Leu Ser Asp Leu Glu Gln Gln Tyr Arg Ala Leu Arg Lys Tyr Tyr Glu
            35                  40                  45

Asn Cys Glu Val Val Met Gly Asn Leu Glu Ile Thr Ser Ile Glu His
50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Arg Thr Val Cys Ala
        195                 200                 205

Glu Gln Cys Asp Gly Arg Cys Tyr Gly Pro Tyr Val Ser Asp Cys Cys
    210                 215                 220

His Arg Glu Cys Ala Gly Gly Cys Ser Gly Pro Lys Asp Thr Asp Cys
```

-continued

```
                225                 230                 235                 240
            Phe Ala Cys Met Asn Phe Asn Asp Ser Gly Ala Cys Val Thr Thr Cys
                            245                 250                 255

Pro Pro Leu Met Leu Tyr Asn Pro Thr Thr Tyr Gln Met Asp Val Asn
                            260                 265                 270

Pro Glu Gly Lys Tyr Ser Phe Gly Ala Thr Cys Val Lys Lys Cys Pro
                            275                 280                 285

Arg Asn Tyr Val Val Thr Asp His Gly Ser Cys Val Arg Ala Cys Gly
                            290                 295                 300

Ala Asp Ser Tyr Glu Met Glu Glu Asp Gly Val Arg Lys Cys Lys Lys
            305                 310                 315                 320

Cys Glu Gly Pro Cys Arg Lys Val Cys Asn Gly Ile Gly Ile Gly Glu
                            325                 330                 335

Phe Lys Asp Ser Leu Ser Ile Asn Ala Thr Asn Ile Lys His Phe Lys
                            340                 345                 350

Asn Cys Thr Ser Ile Ser Gly Asp Leu His Ile Leu Pro Val Ala Phe
                            355                 360                 365

Arg Gly Asp Ser Phe Thr His Thr Pro Pro Leu Asp Pro Gln Glu Leu
                            370                 375                 380

Asp Ile Leu Lys Thr Val Lys Glu Ile Thr Gly Phe Leu Leu Ile Gln
            385                 390                 395                 400

Ala Trp Pro Glu Asn Arg Thr Asp Leu His Ala Phe Glu Asn Leu Glu
                            405                 410                 415

Ile Ile Arg Gly Arg Thr Lys Gln His Gly Gln Phe Ser Leu Ala Val
                            420                 425                 430

Val Ser Leu Asn Ile Thr Ser Leu Gly Leu Arg Ser Leu Lys Glu Ile
                            435                 440                 445

Ser Asp Gly Asp Val Ile Ile Ser Gly Asn Lys Asn Leu Cys Tyr Ala
                            450                 455                 460

Asn Thr Ile Asn Trp Lys Lys Leu Phe Gly Thr Ser Gly Gln Lys Thr
            465                 470                 475                 480

Lys Ile Ile Ser Asn Arg Gly Glu Asn Ser Cys Lys Ala Thr Gly Gln
                            485                 490                 495

Val Cys His Ala Leu Cys Ser Pro Glu Gly Cys Trp Gly Pro Glu Pro
                            500                 505                 510

Arg Asp Cys Val Ser Val Glu Cys Pro Pro Cys Pro Ala Pro Pro Val
                            515                 520                 525

Ala Gly Pro Ser Val Phe Leu Phe Pro Pro Lys Pro Lys Asp Thr Leu
                            530                 535                 540

Met Ile Ser Arg Thr Pro Glu Val Thr Cys Val Val Val Asp Val Ser
            545                 550                 555                 560

His Glu Asp Pro Glu Val Gln Phe Asn Trp Tyr Val Asp Gly Met Glu
                            565                 570                 575

Val His Asn Ala Lys Thr Lys Pro Arg Glu Glu Gln Phe Asn Ser Thr
                            580                 585                 590

Phe Arg Val Val Ser Val Leu Thr Val Val His Gln Asp Trp Leu Asn
                            595                 600                 605

Gly Lys Glu Tyr Lys Cys Lys Val Ser Asn Lys Gly Leu Pro Ala Pro
                            610                 615                 620

Ile Glu Lys Thr Ile Ser Lys Thr Lys Gly Gln Pro Arg Glu Pro Gln
            625                 630                 635                 640

Val Tyr Thr Leu Pro Pro Ser Arg Glu Glu Met Thr Lys Asn Gln Val
                            645                 650                 655
```

```
Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
        740

<210> SEQ ID NO 15
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 15

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Arg Thr Val Cys Ala
        195                 200                 205

Glu Gln Cys Asp Gly Arg Cys Tyr Gly Pro Tyr Val Ser Asp Cys Cys
    210                 215                 220

His Arg Glu Cys Ala Gly Gly Cys Ser Gly Pro Lys Asp Thr Asp Cys
225                 230                 235                 240

Phe Ala Cys Met Asn Phe Asn Asp Ser Gly Ala Cys Val Thr Gln Cys
                245                 250                 255

Pro Gln Thr Phe Val Tyr Asn Pro Thr Thr Phe Gln Leu Glu His Asn
            260                 265                 270
```

```
Phe Asn Ala Lys Tyr Thr Tyr Gly Ala Phe Cys Val Lys Lys Cys Pro
        275                 280                 285

Arg Asn Tyr Val Val Thr Asp His Gly Ser Cys Val Arg Ala Cys Gly
        290                 295                 300

Ala Asp Ser Tyr Glu Met Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
                340                 345                 350

Asn Cys Thr Ser Ile Ser Gly Asp Leu His Ile Leu Pro Val Ala Phe
                355                 360                 365

Arg Gly Asp Ser Phe Thr His Thr Pro Pro Leu Asp Pro Gln Glu Leu
                370                 375                 380

Asp Ile Leu Lys Thr Val Lys Glu Ile Thr Gly Phe Leu Leu Ile Gln
385                 390                 395                 400

Ala Trp Pro Glu Asn Arg Thr Asp Leu His Ala Phe Glu Asn Leu Glu
                405                 410                 415

Ile Ile Arg Gly Arg Thr Lys Gln His Gly Gln Phe Ser Leu Ala Val
                420                 425                 430

Val Ser Leu Asn Ile Thr Ser Leu Gly Leu Arg Ser Leu Lys Glu Ile
                435                 440                 445

Ser Asp Gly Asp Val Ile Ile Ser Gly Asn Lys Asn Leu Cys Tyr Ala
        450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
                500                 505                 510

Arg Asp Cys Val Ser Val Glu Cys Pro Pro Cys Ala Pro Pro Val
        515                 520                 525

Ala Gly Pro Ser Val Phe Leu Phe Pro Pro Lys Pro Lys Asp Thr Leu
        530                 535                 540

Met Ile Ser Arg Thr Pro Glu Val Thr Cys Val Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
                580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
        610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
                660                 665                 670

Glu Trp Glu Ser Asn Gly Gln Pro Glu Asn Asn Tyr Lys Thr Thr Pro
                675                 680                 685
```

```
Pro Met Leu Asp Ser Asp Gly Ser Phe Phe Leu Tyr Ser Lys Leu Thr
            690                 695                 700
Val Asp Lys Ser Arg Trp Gln Gln Gly Asn Val Phe Ser Cys Ser Val
705                 710                 715                 720
Met His Glu Ala Leu His Asn His Tyr Thr Gln Lys Ser Leu Ser Leu
                725                 730                 735
Ser Pro Gly Lys
            740

<210> SEQ ID NO 16
<211> LENGTH: 739
<212> TYPE: PRT
<213> ORGANISM: Artificial Sequence
<220> FEATURE:
<223> OTHER INFORMATION: Hybrid sequence derived from Homo sapien genes

<400> SEQUENCE: 16

Met Glu Trp Ser Trp Val Phe Leu Phe Phe Leu Ser Val Thr Thr Gly
1               5                   10                  15
Val His Ser Gln Ser Val Cys Ala Gly Thr Glu Asn Lys Leu Ser Ser
            20                  25                  30
Leu Ser Asp Leu Glu Gln Gln Tyr Arg Ala Leu Arg Lys Tyr Tyr Glu
        35                  40                  45
Asn Cys Glu Val Val Met Gly Asn Leu Glu Ile Thr Ser Ile Glu His
50                  55                  60
Asn Arg Asp Leu Ser Phe Leu Arg Ser Val Arg Glu Val Thr Gly Tyr
65                  70                  75                  80
Val Leu Val Ala Leu Asn Gln Phe Arg Tyr Leu Pro Leu Glu Asn Leu
                85                  90                  95
Arg Ile Ile Arg Gly Thr Lys Leu Tyr Glu Asp Arg Tyr Ala Leu Ala
            100                 105                 110
Ile Phe Leu Asn Tyr Arg Lys Asp Gly Asn Phe Gly Leu Gln Glu Leu
        115                 120                 125
Gly Leu Lys Asn Leu Thr Glu Ile Leu Asn Gly Gly Val Tyr Val Asp
130                 135                 140
Gln Asn Lys Phe Leu Cys Tyr Ala Asp Thr Ile His Trp Gln Asp Ile
145                 150                 155                 160
Val Arg Asn Pro Trp Pro Ser Asn Leu Thr Leu Val Ser Thr Asn Gly
                165                 170                 175
Ser Ser Gly Cys Gly Arg Cys His Lys Ser Cys Thr Gly Arg Cys Trp
            180                 185                 190
Gly Pro Thr Glu Asn His Cys Gln Thr Leu Thr Arg Thr Val Cys Ala
        195                 200                 205
Glu Gln Cys Asp Gly Arg Cys Tyr Gly Pro Tyr Val Ser Asp Cys Cys
    210                 215                 220
His Arg Glu Cys Ala Gly Gly Cys Ser Gly Pro Lys Asp Thr Asp Cys
225                 230                 235                 240
Phe Ala Cys Met Asn Phe Asn Asp Ser Gly Ala Cys Val Thr Gln Cys
                245                 250                 255
Pro Gln Thr Phe Val Tyr Asn Pro Thr Thr Phe Gln Leu Glu His Asn
            260                 265                 270
Phe Asn Ala Lys Tyr Thr Tyr Gly Ala Phe Cys Val Lys Lys Cys Pro
        275                 280                 285
His Asn Phe Val Val Asp Ser Ser Ser Cys Val Arg Ala Cys Gly Ala
    290                 295                 300
```

```
Asp Ser Tyr Glu Met Glu Glu Asp Gly Val Arg Lys Cys Lys Lys Cys
305                 310                 315                 320

Glu Gly Pro Cys Arg Lys Val Cys Asn Gly Ile Gly Ile Gly Glu Phe
            325                 330                 335

Lys Asp Ser Leu Ser Ile Asn Ala Thr Asn Ile Lys His Phe Lys Asn
                340                 345                 350

Cys Thr Ser Ile Ser Gly Asp Leu His Ile Leu Pro Val Ala Phe Arg
                355                 360                 365

Gly Asp Ser Phe Thr His Thr Pro Leu Asp Pro Gln Glu Leu Asp
370                 375                 380

Ile Leu Lys Thr Val Lys Glu Ile Thr Gly Phe Leu Leu Ile Gln Ala
385                 390                 395                 400

Trp Pro Glu Asn Arg Thr Asp Leu His Ala Phe Glu Asn Leu Glu Ile
                405                 410                 415

Ile Arg Gly Arg Thr Lys Gln His Gly Gln Phe Ser Leu Ala Val Val
                420                 425                 430

Ser Leu Asn Ile Thr Ser Leu Gly Leu Arg Ser Leu Lys Glu Ile Ser
                435                 440                 445

Asp Gly Asp Val Ile Ile Ser Gly Asn Lys Asn Leu Cys Tyr Ala Asn
450                 455                 460

Thr Ile Asn Trp Lys Lys Leu Phe Gly Thr Ser Gly Gln Lys Thr Lys
465                 470                 475                 480

Ile Ile Ser Asn Arg Gly Glu Asn Ser Cys Lys Ala Thr Gly Gln Val
                485                 490                 495

Cys His Ala Leu Cys Ser Pro Glu Gly Cys Trp Gly Pro Glu Pro Arg
            500                 505                 510

Asp Cys Val Ser Val Glu Cys Pro Cys Pro Ala Pro Pro Val Ala
            515                 520                 525

Gly Pro Ser Val Phe Leu Phe Pro Pro Lys Pro Lys Asp Thr Leu Met
            530                 535                 540

Ile Ser Arg Thr Pro Glu Val Thr Cys Val Val Val Asp Val Ser His
545                 550                 555                 560

Glu Asp Pro Glu Val Gln Phe Asn Trp Tyr Val Asp Gly Met Glu Val
                565                 570                 575

His Asn Ala Lys Thr Lys Pro Arg Glu Glu Gln Phe Asn Ser Thr Phe
            580                 585                 590

Arg Val Val Ser Val Leu Thr Val Val His Gln Asp Trp Leu Asn Gly
            595                 600                 605

Lys Glu Tyr Lys Cys Lys Val Ser Asn Lys Gly Leu Pro Ala Pro Ile
610                 615                 620

Glu Lys Thr Ile Ser Lys Thr Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
            660                 665                 670

Trp Glu Ser Asn Gly Gln Pro Glu Asn Asn Tyr Lys Thr Thr Pro Pro
            675                 680                 685

Met Leu Asp Ser Asp Gly Ser Phe Phe Leu Tyr Ser Lys Leu Thr Val
            690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
```

Pro Gly Lys

<210> SEQ ID NO 17
<211> LENGTH: 739
<212> TYPE: PRT
<213> ORGANISM: Artificial Sequence
<220> FEATURE:
<223> OTHER INFORMATION: Hybrid sequence derived from Homo sapien genes

<400> SEQUENCE: 17

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Arg Thr Val Cys Ala
        195                 200                 205

Glu Gln Cys Asp Gly Arg Cys Tyr Gly Pro Tyr Val Ser Asp Cys Cys
    210                 215                 220

His Arg Glu Cys Ala Gly Gly Cys Ser Gly Pro Lys Asp Thr Asp Cys
225                 230                 235                 240

Phe Ala Cys Met Asn Phe Asn Asp Ser Gly Ala Cys Val Thr Gln Cys
                245                 250                 255

Pro Gln Thr Phe Val Tyr Asn Pro Thr Thr Phe Gln Leu Glu His Asn
            260                 265                 270

Phe Asn Ala Lys Tyr Thr Tyr Gly Ala Phe Cys Val Lys Lys Cys Pro
        275                 280                 285

His Asn Phe Val Val Asp Ser Ser Ser Cys Val Arg Ala Cys Pro Ser
    290                 295                 300

Ser Lys Met Glu Val Glu Glu Asn Gly Ile Lys Met Cys Lys Pro Cys
305                 310                 315                 320

Glu Gly Pro Cys Arg Lys Val Cys Asn Gly Ile Gly Ile Gly Glu Phe
                325                 330                 335

Lys Asp Ser Leu Ser Ile Asn Ala Thr Asn Ile Lys His Phe Lys Asn
            340                 345                 350

```
Cys Thr Ser Ile Ser Gly Asp Leu His Ile Leu Pro Val Ala Phe Arg
        355                 360                 365

Gly Asp Ser Phe Thr His Thr Pro Leu Asp Pro Gln Glu Leu Asp
        370                 375                 380

Ile Leu Lys Thr Val Lys Glu Ile Thr Gly Phe Leu Leu Ile Gln Ala
385                 390                 395                 400

Trp Pro Glu Asn Arg Thr Asp Leu His Ala Phe Glu Asn Leu Glu Ile
                405                 410                 415

Ile Arg Gly Arg Thr Lys Gln His Gly Gln Phe Ser Leu Ala Val Val
                420                 425                 430

Ser Leu Asn Ile Thr Ser Leu Gly Leu Arg Ser Leu Lys Glu Ile Ser
        435                 440                 445

Asp Gly Asp Val Ile Ile Ser Gly Asn Lys Asn Leu Cys Tyr Ala Asn
        450                 455                 460

Thr Ile Asn Trp Lys Lys Leu Phe Gly Thr Ser Gly Gln Lys Thr Lys
465                 470                 475                 480

Ile Ile Ser Asn Arg Gly Glu Asn Ser Cys Lys Ala Thr Gly Gln Val
                485                 490                 495

Cys His Ala Leu Cys Ser Pro Glu Gly Cys Trp Gly Pro Glu Pro Arg
        500                 505                 510

Asp Cys Val Ser Val Glu Cys Pro Pro Cys Pro Ala Pro Pro Val Ala
        515                 520                 525

Gly Pro Ser Val Phe Leu Phe Pro Pro Lys Pro Lys Asp Thr Leu Met
        530                 535                 540

Ile Ser Arg Thr Pro Glu Val Thr Cys Val Val Val Asp Val Ser His
545                 550                 555                 560

Glu Asp Pro Glu Val Gln Phe Asn Trp Tyr Val Asp Gly Met Glu Val
                565                 570                 575

His Asn Ala Lys Thr Lys Pro Arg Glu Glu Gln Phe Asn Ser Thr Phe
                580                 585                 590

Arg Val Val Ser Val Leu Thr Val Val His Gln Asp Trp Leu Asn Gly
        595                 600                 605

Lys Glu Tyr Lys Cys Lys Val Ser Asn Lys Gly Leu Pro Ala Pro Ile
        610                 615                 620

Glu Lys Thr Ile Ser Lys Thr Lys Gly Gln Pro Arg Glu Pro Gln Val
625                 630                 635                 640

Tyr Thr Leu Pro Pro Ser Arg Glu Glu Met Thr Lys Asn Gln Val Ser
                645                 650                 655

Leu Thr Cys Leu Val Lys Gly Phe Tyr Pro Ser Asp Ile Ala Val Glu
        660                 665                 670

Trp Glu Ser Asn Gly Gln Pro Glu Asn Asn Tyr Lys Thr Thr Pro Pro
        675                 680                 685

Met Leu Asp Ser Asp Gly Ser Phe Phe Leu Tyr Ser Lys Leu Thr Val
        690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
                725                 730                 735

Pro Gly Lys

<210> SEQ ID NO 18
<211> LENGTH: 740
<212> TYPE: PRT
```

<213> ORGANISM: Artificial Sequence
<220> FEATURE:
<223> OTHER INFORMATION: Hybrid sequence derived from Homo sapien genes

<400> SEQUENCE: 18

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Lys Ile Ile Cys Ala
        195                 200                 205

Gln Gln Cys Ser Gly Arg Cys Arg Gly Lys Ser Pro Ser Asp Cys Cys
    210                 215                 220

His Asn Gln Cys Ala Ala Gly Cys Thr Gly Pro Arg Glu Ser Asp Cys
225                 230                 235                 240

Leu Val Cys Arg Lys Phe Arg Asp Glu Ala Thr Cys Lys Asp Thr Cys
                245                 250                 255

Pro Pro Leu Met Leu Tyr Asn Pro Thr Thr Tyr Gln Met Asp Val Asn
            260                 265                 270

Pro Glu Gly Lys Tyr Ser Phe Gly Ala Thr Cys Val Lys Lys Cys Pro
        275                 280                 285

Arg Asn Tyr Val Val Thr Asp His Gly Ser Cys Val Arg Ala Cys Gly
    290                 295                 300

Ala Asp Ser Tyr Glu Met Glu Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
            340                 345                 350

Asn Cys Thr Ser Ile Ser Gly Asp Leu His Ile Leu Pro Val Ala Phe
        355                 360                 365

Arg Gly Asp Ser Phe Thr His Thr Pro Pro Leu Asp Pro Gln Glu Leu
    370                 375                 380

Asp Ile Leu Lys Thr Val Lys Glu Ile Thr Gly Phe Leu Leu Ile Gln

```
              385                 390                 395                 400
Ala Trp Pro Glu Asn Arg Thr Asp Leu His Ala Phe Glu Asn Leu Glu
                    405                 410                 415

Ile Ile Arg Gly Arg Thr Lys Gln His Gly Gln Phe Ser Leu Ala Val
                420                 425                 430

Val Ser Leu Asn Ile Thr Ser Leu Gly Leu Arg Ser Leu Lys Glu Ile
            435                 440                 445

Ser Asp Gly Asp Val Ile Ile Ser Gly Asn Lys Asn Leu Cys Tyr Ala
        450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
            500                 505                 510

Arg Asp Cys Val Ser Val Glu Cys Pro Pro Cys Pro Ala Pro Pro Val
        515                 520                 525

Ala Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
    610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 19
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 19

Met Glu Trp Ser Trp Val Phe Leu Phe Phe Leu Ser Val Thr Thr Gly
```

-continued

```
1               5                   10                  15
Val His Ser Gln Ser Val Cys Ala Gly Thr Glu Asn Lys Leu Ser Ser
            20                  25                  30
Leu Ser Asp Leu Glu Gln Gln Tyr Arg Ala Leu Arg Lys Tyr Tyr Glu
            35                  40                  45
Asn Cys Glu Val Val Met Gly Asn Leu Glu Ile Thr Ser Ile Glu His
            50                  55                  60
Asn Arg Asp Leu Ser Phe Leu Arg Ser Val Arg Glu Val Thr Gly Tyr
65                  70                  75                  80
Val Leu Val Ala Leu Asn Gln Phe Arg Tyr Leu Pro Leu Glu Asn Leu
            85                  90                  95
Arg Ile Ile Arg Gly Thr Lys Leu Tyr Glu Asp Arg Tyr Ala Leu Ala
            100                 105                 110
Ile Phe Leu Asn Tyr Arg Lys Asp Gly Asn Phe Gly Leu Gln Glu Leu
            115                 120                 125
Gly Leu Lys Asn Leu Thr Glu Ile Leu Asn Gly Gly Val Tyr Val Asp
            130                 135                 140
Gln Asn Lys Phe Leu Cys Tyr Ala Asp Thr Ile His Trp Gln Asp Ile
145                 150                 155                 160
Val Arg Asn Pro Trp Pro Ser Asn Leu Thr Leu Val Ser Thr Asn Gly
            165                 170                 175
Ser Ser Gly Cys Gly Arg Cys His Lys Ser Cys Thr Gly Arg Cys Trp
            180                 185                 190
Gly Pro Thr Glu Asn His Cys Gln Thr Leu Thr Arg Thr Val Cys Ala
            195                 200                 205
Glu Gln Cys Asp Gly Arg Cys Tyr Gly Pro Tyr Val Ser Asp Cys Cys
            210                 215                 220
His Arg Glu Cys Ala Gly Gly Cys Ser Gly Pro Lys Asp Thr Asp Cys
225                 230                 235                 240
Phe Ala Cys Met Asn Phe Asn Asp Ser Gly Ala Cys Val Thr Gln Cys
            245                 250                 255
Pro Gln Thr Phe Val Tyr Asn Pro Thr Thr Tyr Gln Met Asp Val Asn
            260                 265                 270
Pro Glu Gly Lys Tyr Ser Phe Gly Ala Thr Cys Val Lys Lys Cys Pro
            275                 280                 285
Arg Asn Tyr Val Val Thr Asp His Gly Ser Cys Val Arg Ala Cys Gly
            290                 295                 300
Ala Asp Ser Tyr Glu Met Glu Glu Asp Gly Val Arg Lys Cys Lys Lys
305                 310                 315                 320
Cys Glu Gly Pro Cys Arg Lys Val Cys Asn Gly Ile Gly Ile Gly Glu
            325                 330                 335
Phe Lys Asp Ser Leu Ser Ile Asn Ala Thr Asn Ile Lys His Phe Lys
            340                 345                 350
Asn Cys Thr Ser Ile Ser Gly Asp Leu His Ile Leu Pro Val Ala Phe
            355                 360                 365
Arg Gly Asp Ser Phe Thr His Thr Pro Pro Leu Asp Pro Gln Glu Leu
            370                 375                 380
Asp Ile Leu Lys Thr Val Lys Glu Ile Thr Gly Phe Leu Leu Ile Gln
385                 390                 395                 400
Ala Trp Pro Glu Asn Arg Thr Asp Leu His Ala Phe Glu Asn Leu Glu
            405                 410                 415
Ile Ile Arg Gly Arg Thr Lys Gln His Gly Gln Phe Ser Leu Ala Val
            420                 425                 430
```

```
Val Ser Leu Asn Ile Thr Ser Leu Gly Leu Arg Ser Leu Lys Glu Ile
        435                 440                 445

Ser Asp Gly Asp Val Ile Ile Ser Gly Asn Lys Asn Leu Cys Tyr Ala
450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
            500                 505                 510

Arg Asp Cys Val Ser Val Glu Cys Pro Pro Cys Pro Ala Pro Pro Val
                515                 520                 525

Ala Gly Pro Ser Val Phe Leu Phe Pro Pro Lys Pro Lys Asp Thr Leu
            530                 535                 540

Met Ile Ser Arg Thr Pro Glu Val Thr Cys Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
                595                 600                 605

Gly Lys Glu Tyr Lys Cys Lys Val Ser Asn Lys Gly Leu Pro Ala Pro
            610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
                675                 680                 685

Pro Met Leu Asp Ser Asp Gly Ser Phe Phe Leu Tyr Ser Lys Leu Thr
            690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 20
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 20

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45
```

-continued

```
Asn Cys Glu Val Val Met Gly Asn Leu Glu Ile Thr Ser Ile Glu His
 50                      55                      60

Asn Arg Asp Leu Ser Phe Leu Arg Ser Val Arg Glu Val Thr Gly Tyr
 65                  70                      75                      80

Val Leu Val Ala Leu Asn Gln Phe Arg Tyr Leu Pro Leu Glu Asn Leu
                 85                      90                      95

Arg Ile Ile Arg Gly Thr Lys Leu Tyr Glu Asp Arg Tyr Ala Leu Ala
            100                     105                     110

Ile Phe Leu Asn Tyr Arg Lys Asp Gly Asn Phe Gly Leu Gln Glu Leu
        115                     120                     125

Gly Leu Lys Asn Leu Thr Glu Ile Leu Asn Gly Gly Val Tyr Val Asp
    130                     135                     140

Gln Asn Lys Phe Leu Cys Tyr Ala Asp Thr Ile His Trp Gln Asp Ile
145                     150                     155                     160

Val Arg Asn Pro Trp Pro Ser Asn Leu Thr Leu Val Ser Thr Asn Gly
                165                     170                     175

Ser Ser Gly Cys Gly Arg Cys His Lys Ser Cys Thr Gly Arg Cys Trp
            180                     185                     190

Gly Pro Thr Glu Asn His Cys Gln Thr Leu Thr Arg Thr Val Cys Ala
        195                     200                     205

Glu Gln Cys Asp Gly Arg Cys Tyr Gly Pro Tyr Val Ser Asp Cys Cys
    210                     215                     220

His Arg Glu Cys Ala Gly Gly Cys Ser Gly Pro Lys Asp Thr Asp Cys
225                     230                     235                     240

Phe Ala Cys Met Asn Phe Asn Asp Ser Gly Ala Cys Val Thr Gln Cys
                245                     250                     255

Pro Gln Thr Phe Val Tyr Asn Pro Thr Thr Tyr Gln Met Asp Val Asn
            260                     265                     270

Pro Glu Gly Lys Tyr Ser Phe Gly Ala Thr Cys Val Lys Lys Cys Pro
        275                     280                     285

Arg Asn Tyr Val Val Thr Asp His Gly Ser Cys Val Arg Ala Cys Gly
    290                     295                     300

Ala Asp Ser Tyr Glu Met Glu Glu Asp Gly Val Arg Lys Cys Lys Lys
305                     310                     315                     320

Cys Glu Gly Pro Cys Arg Lys Val Cys Asn Gly Ile Gly Ile Gly Glu
                325                     330                     335

Phe Lys Asp Ser Leu Ser Ile Asn Ala Thr Asn Ile Lys His Phe Lys
            340                     345                     350

Asn Cys Thr Ser Ile Ser Gly Asp Leu His Ile Leu Pro Val Ala Phe
        355                     360                     365

Arg Gly Asp Ser Phe Thr His Thr Pro Pro Leu Asp Pro Gln Glu Leu
    370                     375                     380

Asp Ile Leu Lys Thr Val Lys Glu Ile Thr Gly Phe Leu Leu Ile Gln
385                     390                     395                     400

Ala Trp Pro Glu Asn Arg Thr Asp Leu His Ala Phe Glu Asn Leu Glu
                405                     410                     415

Ile Ile Arg Gly Arg Thr Lys Gln His Gly Gln Phe Ser Leu Ala Val
            420                     425                     430

Val Ser Leu Asn Ile Thr Ser Leu Gly Leu Arg Ser Leu Lys Glu Ile
        435                     440                     445

Ser Asp Gly Asp Val Ile Ile Ser Gly Asn Lys Asn Leu Cys Tyr Ala
    450                     455                     460
```

```
Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
            485                 490                 495

Val Cys His Ala Leu Cys Ser Pro Glu Gly Cys Trp Gly Pro Glu Pro
        500                 505                 510

Arg Asp Cys Val Ser Val Glu Ser Pro Ser Pro Ala Pro Pro Val
515                 520                 525

Ala Gly Pro Ser Val Phe Leu Phe Pro Pro Lys Pro Lys Asp Thr Leu
    530                 535                 540

Met Ile Ser Arg Thr Pro Glu Val Thr Cys Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
    610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 21
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 21

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Gln
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80
```

```
Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
                180                 185                 190

Gly Pro Thr Glu Asn His Cys Gln Thr Leu Thr Arg Thr Val Cys Ala
            195                 200                 205

Glu Gln Cys Asp Gly Arg Cys Tyr Gly Pro Tyr Val Ser Asp Cys Cys
        210                 215                 220

His Arg Glu Cys Ala Gly Gly Cys Ser Gly Pro Lys Asp Thr Asp Cys
225                 230                 235                 240

Phe Ala Cys Met Asn Phe Asn Asp Ser Gly Ala Cys Val Thr Gln Cys
                245                 250                 255

Pro Gln Thr Phe Val Tyr Asn Pro Thr Thr Tyr Gln Met Asp Val Asn
                260                 265                 270

Pro Glu Gly Lys Tyr Ser Phe Gly Ala Thr Cys Val Lys Lys Cys Pro
            275                 280                 285

Arg Asn Tyr Val Val Thr Asp His Gly Ser Cys Val Arg Ala Cys Gly
        290                 295                 300

Ala Asp Ser Tyr Glu Met Glu Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
            340                 345                 350

Asn Cys Thr Ser Ile Ser Gly Asp Leu His Ile Leu Pro Val Ala Phe
        355                 360                 365

Arg Gly Asp Ser Phe Thr His Thr Pro Pro Leu Asp Pro Gln Glu Leu
    370                 375                 380

Asp Ile Leu Lys Thr Val Lys Glu Ile Thr Gly Phe Leu Leu Ile Gln
385                 390                 395                 400

Ala Trp Pro Glu Asn Arg Thr Asp Leu His Ala Phe Glu Asn Leu Glu
                405                 410                 415

Ile Ile Arg Gly Arg Thr Lys Gln His Gly Gln Phe Ser Leu Ala Val
            420                 425                 430

Val Ser Leu Asn Ile Thr Ser Leu Gly Leu Arg Ser Leu Lys Glu Ile
        435                 440                 445

Ser Asp Gly Asp Val Ile Ile Ser Gly Asn Lys Asn Leu Cys Tyr Ala
    450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
```

```
                500             505             510
Arg Asp Cys Val Ser Val Glu Ser Pro Pro Ser Pro Ala Pro Pro Val
            515                 520                 525
Ala Gly Pro Ser Val Phe Leu Phe Pro Pro Lys Pro Lys Asp Thr Leu
            530                 535                 540
Met Ile Ser Arg Thr Pro Glu Val Thr Cys Val Val Val Asp Val Ser
545                 550                 555                 560
His Glu Asp Pro Glu Val Gln Phe Asn Trp Tyr Val Asp Gly Met Glu
                565                 570                 575
Val His Asn Ala Lys Thr Lys Pro Arg Glu Glu Gln Phe Asn Ser Thr
            580                 585                 590
Phe Arg Val Val Ser Val Leu Thr Val Val His Gln Asp Trp Leu Asn
            595                 600                 605
Gly Lys Glu Tyr Lys Cys Lys Val Ser Asn Lys Gly Leu Pro Ala Pro
            610                 615                 620
Ile Glu Lys Thr Ile Ser Lys Thr Lys Gly Gln Pro Arg Glu Pro Gln
625                 630                 635                 640
Val Tyr Thr Leu Pro Pro Ser Arg Glu Glu Met Thr Lys Asn Gln Val
                645                 650                 655
Ser Leu Thr Cys Leu Val Lys Gly Phe Tyr Pro Ser Asp Ile Ala Val
            660                 665                 670
Glu Trp Glu Ser Asn Gly Gln Pro Glu Asn Asn Tyr Lys Thr Thr Pro
            675                 680                 685
Pro Met Leu Asp Ser Asp Gly Ser Phe Phe Leu Tyr Ser Lys Leu Thr
            690                 695                 700
Val Asp Lys Ser Arg Trp Gln Gln Gly Asn Val Phe Ser Cys Ser Val
705                 710                 715                 720
Met His Glu Ala Leu His Asn His Tyr Thr Gln Lys Ser Leu Ser Leu
                725                 730                 735
Ser Pro Gly Lys
            740

<210> SEQ ID NO 22
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 22

Met Glu Trp Ser Trp Val Phe Leu Phe Phe Leu Ser Val Thr Thr Gly
1               5                   10                  15
Val His Ser Gln Ser Val Cys Ala Gly Thr Glu Asn Lys Leu Ser Ser
            20                  25                  30
Leu Ser Asp Leu Glu Gln Gln Tyr Arg Ala Leu Arg Lys Tyr Tyr Glu
        35                  40                  45
Asn Cys Glu Val Val Met Gly Asn Leu Glu Ile Thr Tyr Ile Glu His
    50                  55                  60
Asn Arg Asp Leu Ser Phe Leu Arg Ser Val Arg Glu Val Thr Gly Tyr
65                  70                  75                  80
Val Leu Val Ala Leu Asn Gln Phe Arg Tyr Leu Pro Leu Glu Asn Leu
                85                  90                  95
Arg Ile Ile Arg Gly Thr Lys Leu Tyr Glu Asp Arg Tyr Ala Leu Ala
            100                 105                 110
Ile Phe Leu Asn Tyr Arg Lys Asp Gly Asn Phe Gly Leu Gln Glu Leu
```

-continued

```
            115                 120                 125
Gly Leu Lys Asn Leu Thr Glu Ile Leu Asn Gly Gly Val Tyr Val Asp
            130                 135                 140
Gln Asn Lys Phe Leu Cys Tyr Ala Asp Thr Ile His Trp Gln Asp Ile
145                 150                 155                 160
Val Arg Asn Pro Trp Pro Ser Asn Leu Thr Leu Val Ser Thr Asn Gly
                    165                 170                 175
Ser Ser Gly Cys Gly Arg Cys His Lys Ser Cys Thr Gly Arg Cys Trp
                180                 185                 190
Gly Pro Thr Glu Asn His Cys Gln Thr Leu Thr Arg Thr Val Cys Ala
                    195                 200                 205
Glu Gln Cys Asp Gly Arg Cys Tyr Gly Pro Tyr Val Ser Asp Cys Cys
            210                 215                 220
His Arg Glu Cys Ala Gly Gly Cys Ser Gly Pro Lys Asp Thr Asp Cys
225                 230                 235                 240
Phe Ala Cys Met Asn Phe Asn Asp Ser Gly Ala Cys Val Thr Gln Cys
                    245                 250                 255
Pro Gln Thr Phe Val Tyr Asn Pro Thr Thr Tyr Gln Met Asp Val Asn
                260                 265                 270
Pro Glu Gly Lys Tyr Ser Phe Gly Ala Thr Cys Val Lys Lys Cys Pro
                275                 280                 285
Arg Asn Tyr Val Val Thr Asp His Gly Ser Cys Val Arg Ala Cys Gly
            290                 295                 300
Ala Asp Ser Tyr Glu Met Glu Glu Asp Gly Val Arg Lys Cys Lys Lys
305                 310                 315                 320
Cys Glu Gly Pro Cys Arg Lys Val Cys Asn Gly Ile Gly Ile Gly Glu
                    325                 330                 335
Phe Lys Asp Ser Leu Ser Ile Asn Ala Thr Asn Ile Lys His Phe Lys
                340                 345                 350
Asn Cys Thr Ser Ile Ser Gly Asp Leu His Ile Leu Pro Val Ala Phe
                355                 360                 365
Arg Gly Asp Ser Phe Thr His Thr Pro Pro Leu Asp Pro Gln Glu Leu
            370                 375                 380
Asp Ile Leu Lys Thr Val Lys Glu Ile Thr Gly Phe Leu Leu Ile Gln
385                 390                 395                 400
Ala Trp Pro Glu Asn Arg Thr Asp Leu His Ala Phe Glu Asn Leu Glu
                    405                 410                 415
Ile Ile Arg Gly Arg Thr Lys Gln His Gly Gln Phe Ser Leu Ala Val
                420                 425                 430
Val Ser Leu Asn Ile Thr Ser Leu Gly Leu Arg Ser Leu Lys Glu Ile
            435                 440                 445
Ser Asp Gly Asp Val Ile Ile Ser Gly Asn Lys Asn Leu Cys Tyr Ala
        450                 455                 460
Asn Thr Ile Asn Trp Lys Lys Leu Phe Gly Thr Ser Gly Gln Lys Thr
465                 470                 475                 480
Lys Ile Ile Ser Asn Arg Gly Glu Asn Ser Cys Lys Ala Thr Gly Gln
                    485                 490                 495
Val Cys His Ala Leu Cys Ser Pro Glu Gly Cys Trp Gly Pro Glu Pro
                500                 505                 510
Arg Asp Cys Val Ser Val Glu Ser Pro Ser Pro Ala Pro Pro Val
            515                 520                 525
Ala Gly Pro Ser Val Phe Leu Phe Pro Pro Lys Pro Lys Asp Thr Leu
        530                 535                 540
```

```
Met Ile Ser Arg Thr Pro Glu Val Thr Cys Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
    610                 615                 620

Ile Glu Lys Thr Ile Ser Lys Thr Lys Gly Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 23
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 23

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Arg Val Asp
    130                 135                 140

Gln Asn Lys Phe Leu Cys Tyr Ala Asp Thr Ile His Trp Gln Asp Ile
145                 150                 155                 160
```

```
Val Arg Asn Pro Trp Pro Ser Asn Leu Thr Leu Val Ser Thr Asn Gly
            165                 170                 175

Ser Ser Gly Cys Gly Arg Cys His Lys Ser Cys Thr Gly Arg Cys Trp
            180                 185                 190

Gly Pro Thr Glu Asn His Cys Gln Thr Leu Thr Arg Thr Val Cys Ala
            195                 200                 205

Glu Gln Cys Asp Gly Arg Cys Tyr Gly Pro Tyr Val Ser Asp Cys Cys
        210                 215                 220

His Arg Glu Cys Ala Gly Cys Ser Gly Pro Lys Asp Thr Asp Cys
225                 230                 235                 240

Phe Ala Cys Met Asn Phe Asn Asp Ser Gly Ala Cys Val Thr Gln Cys
                245                 250                 255

Pro Gln Thr Phe Val Tyr Asn Pro Thr Thr Tyr Gln Met Asp Val Asn
            260                 265                 270

Pro Glu Gly Lys Tyr Ser Phe Gly Ala Thr Cys Val Lys Lys Cys Pro
        275                 280                 285

Arg Asn Tyr Val Val Thr Asp His Gly Ser Cys Val Arg Ala Cys Gly
        290                 295                 300

Ala Asp Ser Tyr Glu Met Glu Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
            340                 345                 350

Asn Cys Thr Ser Ile Ser Gly Asp Leu His Ile Leu Pro Val Ala Phe
        355                 360                 365

Arg Gly Asp Ser Phe Thr His Thr Pro Pro Leu Asp Pro Gln Glu Leu
    370                 375                 380

Asp Ile Leu Lys Thr Val Lys Glu Ile Thr Gly Phe Leu Leu Ile Gln
385                 390                 395                 400

Ala Trp Pro Glu Asn Arg Thr Asp Leu His Ala Phe Glu Asn Leu Glu
                405                 410                 415

Ile Ile Arg Gly Arg Thr Lys Gln His Gly Gln Phe Ser Leu Ala Val
            420                 425                 430

Val Ser Leu Asn Ile Thr Ser Leu Gly Leu Arg Ser Leu Lys Glu Ile
        435                 440                 445

Ser Asp Gly Asp Val Ile Ile Ser Gly Asn Lys Asn Leu Cys Tyr Ala
    450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
            500                 505                 510

Arg Asp Cys Val Ser Val Glu Ser Pro Ser Pro Ala Pro Pro Val
        515                 520                 525

Ala Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Gln Phe Asn Trp Tyr Val Asp Gly Met Glu
                565                 570                 575
```

```
Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
    610                 615                 620

Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Met Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 24
<211> LENGTH: 740
<212> TYPE: PRT
<213> ORGANISM: Artificial Sequence
<220> FEATURE:
<223> OTHER INFORMATION: Hybrid sequence derived from Homo sapien genes

<400> SEQUENCE: 24

Met Glu Trp Ser Trp Val Phe Leu Phe Phe Leu Ser Val Thr Thr Gly
1               5                   10                  15

Val His Ser Gln Ser Val Cys Ala Gly Thr Glu Asn Lys Leu Ser Ser
            20                  25                  30

Leu Ser Asp Leu Glu Gln Gln Tyr Arg Ala Leu Arg Lys Tyr Tyr Glu
        35                  40                  45

Asn Cys Glu Val Val Met Gly Asn Leu Glu Ile Thr Ser Ile Glu His
    50                  55                  60

Asn Arg Asp Leu Ser Phe Leu Arg Ser Val Arg Glu Val Thr Gly Tyr
65                  70                  75                  80

Val Leu Val Ala Leu Asn Gln Phe Arg Tyr Leu Pro Leu Glu Asn Leu
                85                  90                  95

Arg Ile Ile Arg Gly Thr Lys Leu Tyr Glu Asp Arg Tyr Ala Leu Ala
            100                 105                 110

Ile Phe Leu Asn Tyr Arg Lys Asp Gly Asn Phe Gly Leu Gln Glu Leu
        115                 120                 125

Gly Leu Lys Asn Leu Thr Glu Ile Leu Asn Gly Gly Val Tyr Val Asp
    130                 135                 140

Gln Asn Lys Phe Leu Cys Tyr Ala Asp Thr Ile His Trp Gln Asp Ile
145                 150                 155                 160

Val Arg Asn Pro Trp Pro Ser Asn Leu Thr Leu Val Ser Thr Asn Gly
                165                 170                 175

Ser Ser Gly Cys Gly Arg Cys His Lys Ser Cys Thr Gly Arg Cys Trp
            180                 185                 190
```

```
Gly Pro Thr Glu Asn His Cys Gln Thr Leu Thr Lys Ile Ile Cys Ala
            195                 200                 205

Gln Gln Cys Ser Gly Arg Cys Arg Gly Lys Ser Pro Ser Asp Cys Cys
    210                 215                 220

His Asn Gln Cys Ala Ala Gly Cys Thr Gly Pro Arg Glu Ser Asp Cys
225                 230                 235                 240

Leu Val Cys Arg Lys Phe Arg Asp Glu Ala Thr Cys Lys Asp Thr Cys
                245                 250                 255

Pro Pro Leu Met Leu Tyr Asn Pro Thr Thr Tyr Gln Met Asp Val Asn
            260                 265                 270

Pro Glu Gly Lys Tyr Ser Phe Gly Ala Thr Cys Val Lys Lys Cys Pro
        275                 280                 285

Arg Asn Tyr Val Val Thr Asp His Gly Ser Cys Val Arg Ala Cys Gly
    290                 295                 300

Ala Asp Ser Tyr Glu Met Glu Glu Asp Gly Val Arg Lys Cys Lys Lys
305                 310                 315                 320

Cys Glu Gly Pro Cys Arg Lys Val Cys Asn Gly Ile Gly Ile Gly Glu
                325                 330                 335

Phe Lys Asp Ser Leu Ser Ile Asn Ala Thr Asn Ile Lys His Phe Lys
            340                 345                 350

Asn Cys Thr Ser Ile Ser Gly Asp Leu His Ile Leu Pro Val Ala Phe
        355                 360                 365

Arg Gly Asp Ser Phe Thr His Thr Pro Pro Leu Asp Pro Gln Glu Leu
    370                 375                 380

Asp Ile Leu Lys Thr Val Lys Glu Ile Thr Gly Phe Leu Leu Ile Gln
385                 390                 395                 400

Ala Trp Pro Glu Asn Arg Thr Asp Leu His Ala Phe Glu Asn Leu Glu
                405                 410                 415

Ile Ile Arg Gly Arg Thr Lys Gln His Gly Gln Phe Ser Leu Ala Val
            420                 425                 430

Val Ser Leu Asn Ile Thr Ser Leu Gly Leu Arg Ser Leu Lys Glu Ile
        435                 440                 445

Ser Asp Gly Asp Val Ile Ile Ser Gly Asn Lys Asn Leu Cys Tyr Ala
    450                 455                 460

Asn Thr Ile Asn Trp Lys Lys Leu Phe Gly Thr Ser Gly Gln Lys Thr
465                 470                 475                 480

Lys Ile Ile Ser Asn Arg Gly Glu Asn Ser Cys Lys Ala Thr Gly Gln
                485                 490                 495

Val Cys His Ala Leu Cys Ser Pro Glu Gly Cys Trp Gly Pro Glu Pro
            500                 505                 510

Arg Asp Cys Val Ser Val Glu Ser Pro Pro Ser Pro Ala Pro Pro Val
        515                 520                 525

Ala Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560

His Glu Asp Pro Glu Val Gln Phe Asn Trp Tyr Val Asp Gly Met Glu
                565                 570                 575

Val His Asn Ala Lys Thr Lys Pro Arg Glu Glu Gln Phe Asn Ser Thr
            580                 585                 590

Phe Arg Val Val Ser Val Leu Thr Val Val His Gln Asp Trp Leu Asn
        595                 600                 605

Gly Lys Glu Tyr Lys Cys Lys Val Ser Asn Lys Gly Leu Pro Ala Pro
```

```
                     610                 615                 620
Ile Glu Lys Thr Ile Ser Lys Thr Lys Gly Gln Pro Arg Glu Pro Gln
625                 630                 635                 640

Val Tyr Thr Leu Pro Pro Ser Arg Glu Glu Met Thr Lys Asn Gln Val
                645                 650                 655

Ser Leu Thr Cys Leu Val Lys Gly Phe Tyr Pro Ser Asp Ile Ala Val
                660                 665                 670

Glu Trp Glu Ser Asn Gly Gln Pro Glu Asn Asn Tyr Lys Thr Thr Pro
                675                 680                 685

Pro Met Leu Asp Ser Asp Gly Ser Phe Phe Leu Tyr Ser Lys Leu Thr
                690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
                740
```

US 9,051,388 B2

BROAD SPECTRUM ERBB LIGAND BINDING MOLECULES AND METHODS FOR PREPARING AND USING THEM

PRIORITY CLAIM

This application is a continuation of PCT Application Serial No. PCT/US2010/043533, filed 28 Jul. 2010; which claims priority to U.S. Provisional Application No. 61/229,224, filed 28 Jul. 2009; and U.S. Provisional Application No. 61/286,265, filed 14 Dec. 2009.

BACKGROUND

Receptor tyrosine kinases are involved in stimulating the growth of many cancers. In general, receptor tyrosine kinases are glycoproteins which consist of (1) an extracellular domain that is able to bind with a specific ligand, (2) a transmembrane region, (3) a juxtamembrane domain which may regulate the receptor activity by, for instance, protein phosphorylation, (4) a tyrosine kinase domain that is the enzymatic component of the receptor, and (5) a carboxyterminal tail. The ErbB family of type I receptor tyrosine kinases constitute one important class of receptors because of their importance in mediating cell growth, differentiation and survival in many solid tumors. Members of this receptor family include ErbB1 (also known as HER1), ErbB2 (HER2/neu), ErbB3 (HER3), and ErbB4 (HER4). More than a dozen ligands interact with the ErbB-family receptors. For example, EGF, Transforming Growth Factor α (TGFα), and amphiregulin all bind to ErbB1. Isoforms of neuregulin, also known as Heregulin and Neu Differentiation Factor (NDF) have specific affinity for ErbB3 and ErbB4. Ligands such as betacellulin, heparin-binding EGF and epiregulin bind to both ErbB1 and ErbB4.

It is becoming clear that over expression of ErbB activating ligands can cause uncontrolled cellular proliferation similar to that of a deregulated receptor. In such cases, interference with the binding of the activating ligand to its receptor may provide an effective therapeutic strategy or that could accentuate current receptor based or other therapies. Therapeutics that interfere with ligand binding to ErbB3 may be particularly effective. ErbB3 differs from the other receptors in the EGFR family because its tyrosine kinase domain is functionally inactive; however, ErbB2/ErbB3 heterodimers transmit the most potent mitogenic signals of any homo- or heterodimer combination of the ErbB family. Therefore, ErbB3 is an important target, yet one that cannot be inhibited through small molecules that target the kinase region. Since ErbB3 requires an activating ligand, such as heregulin or NDF, before activated heterodimers can form, molecules that can interfere with the binding of ErbB3 receptor ligands could be used to block or interfere with the formation of ErbB dimers and heterodimers. One example of such a molecule would be a molecule that has ligand binding affinity and can therefore "trap" ligands and effectively reduce their concentration so that they cannot activate the ErbB3 receptor. In addition to ErbB3 ligands, the other known ErbB receptor ligands, have similar effects to varying degrees. Thus, binding molecules that can trap and sequester the full spectrum of ErbB ligands may be of even more use in the treatment of cancer.

Several therapeutics exist that have attempted this trapping or "decoy" strategy. For example, Enbrel™ (etanercept—Amgen) is a soluble, modified version of the TNFR receptor that binds and traps the pro-inflammatory ligand TNFα. In addition, a soluble fusion protein of the VEGFR1 and VEGFR2 receptors, called a VEGF Trap, is currently in clinical trials for the treatment of both macular degeneration and several forms of cancer (Regeneron Pharmaceuticals). An ErbB3 trap has also shown potency in vitro at enhancing the effects of a dual EGFR/ErbB2 inhibitor and reversed GW2974 (a small molecule inhibitor of ErbB1 and ErbB2) resistance in cells treated with NDF.

All currently approved ErbB inhibitors target either EGFR, ErbB2, ErbB3, ErbB4 or combinations of all 4 receptors. However, no therapeutic is known that interferes with the binding of ligands to multiple ErbB receptors simultaneously. Clearly, new binding molecules are needed that can be used to sequester receptor ligands, such as ErbB ligands, and thereby block ligand binding to multiple ErbB receptors and subsequent receptor activation. Binding molecules capable of binding all known ErbB ligands would be particularly useful.

A number of binding studies have been carried out to determine regions of ErbB3 that are important to the binding of its ligand, heregulin. Singer, et. al. (2001), *J. Biol. Chem.* 276, 44266-44274. Other studies using chimeric receptors have identified the relative contributions of the extracellular domains of ErbB1 and ErbB4 to ligand-specific signaling. Kim, et. al. (2002), *Eur. J. Biochem.* 269, 2323-2329. These studies reveal that neuregulin binding to ErbB4 depends much more on domain I than on domain III and that domain III of ErbB1 is primarily important for EGF binding. However, these studies were conducted on full length receptors which span the entire length of the receptors including the transmembrane and cytoplasmic domains. These large molecules present manufacturing and administration problems potentially leading to lower therapeutic efficacy.

SUMMARY

Chimeric ErbB ligand binding molecules having detectable binding activity for more ErbB ligands than any one of native ErbB1, ErbB3 or ErbB4 are disclosed. Preferably, the binding molecules bind a broad spectrum and, more preferably, the full spectrum of ErbB ligands. The chimeric ErbB ligand binding molecule generally has a subdomain LI derived from one of ErbB3 or 4 and a subdomain LII derived from another distinct ErbB receptor type, such as ErbB1, which are linked. The sub-domain, SI, can be used to join LI and LII. Subdomain SI can be from either one of the receptor types or can have portions from both.

In one embodiment the chimeric ErbB ligand binding molecule can include at least a portion of LI from ErbB4 linked to at least a portion of LII derived from ErbB1. LII can be linked to module 1 of SII from ErbB1. An SI subdomain can be used to link LI and LII subdomains and can be derived from either the ErbB1 or ErbB4 receptor sequences or can be a mixture of both. Optionally, the ErbB chimera can be fused to an aggregant such as IgG2Fc.

In one embodiment the chimeric ErbB ligand binding molecule can include at least a portion of LI from ErbB4; an SI region having a portion derived from ErbB4 and a portion derived from ErbB1, wherein the ErbB4 portion switches to the ErbB1 portion in a region having homology between the two sequences; at least a portion of LII can be derived from ErbB1 and module 1 of SII of ErbB1.

In one embodiment the chimeric ErbB ligand binding molecule can include at least a portion of a subunit LI from ErbB3 linked to at least a portion of an LII derived from ErbB1 and module 1 of SII from ErbB1. The linking region can be an SI domain from ErbB1, ErbB3 or their mixtures.

In one embodiment the chimeric ErbB ligand binding molecule can include at least a portion of a subunit LI from ErbB3, an SI region having a portion is derived from ErbB3 and a portion is derived from ErbB1, at least a portion of LII derived from ErbB1 and module 1 of SII derived from ErbB1.

In one embodiment the chimeric ErbB ligand binding molecule can include at least a portion of a subunit LI from ErbB4, an SI region having a portion derived from ErbB4 and a portion is derived from ErbB1, at least a portion of LII from ErbB1 and module 1 of SII from ErbB1.

In one embodiment the chimeric ErbB ligand binding molecule can include at least a portion of a subunit LI from ErbB3; an SI region having a portion derived from ErbB3 and a portion derived from ErbB1, wherein the ErbB3 portion switches to the ErbB1 portion in a region having homology between the two sequences; at least a portion of LII derived from ErbB1 and module 1 of SII derived from ErbB1.

DNA sequences that encode the disclosed chimeric ErbB ligand binding Molecules are also contemplated along with sequences that facilitate expression and host cells for the maintenance and expression of such DNA sequences.

Pharmaceutical compositions that contain the chimeric ErbB ligand binding molecules and a pharmaceutically acceptable excipient are also contemplated.

The chimeric ErbB ligand binding molecule can be used by immobilizing it on a solid support which can in turn be used for binding ErbB ligands such that the ligands can be removed from biological fluids, particularly from patients suffering from diseases associated with over-expression of such ligands. The ErbB ligand depleted biological fluids can then be replaced in those patients.

Methods for treating patients having diseases that are associated with overexpression of ErbB ligands are also contemplated that involve administering a pharmaceutical composition that contain therapeutically effective amounts of the chimeric ErbB ligand binding molecule in a pharmaceutically acceptable excipient.

FIGURES

FIG. 1 illustrates several potential subunit structures of a chimeric ErbB4-ErbB1 chimera. The highlighted sequence shows one specific embodiment of a chimeric ErbB ligand binding molecule starting with the ErbB4 sequence.

FIG. 2 illustrates several potential subunit structures of a chimeric ErbB3-ErbB1 chimera.

FIG. 3 provides an alignment of ErbB1 (bottom sequence) and ErbB4 (top sequence). The highlighted amino acid sequence shows one specific embodiment of a chimeric ErbB ligand binding molecule starting with the ErbB sequence.

DETAILED DESCRIPTION

The complete nucleotide sequences of the ErbB1, ErbB2, ErbB3 and ErbB4 are known and can be found in Genbank as accession number NM 005228 for ErbB1, accession number NM 004448 for ErbB2, accession number M29366 or NM 001982 for ErbB3, and accession number NM 005235 for ErbB4. The full length ectodomain, the extracellular domain, for ErbB receptors contains four sub-domains, sometimes referred to as L1, CR1, L2 and CR2, where L and CR stand for large and cysteine rich, respectively. The sub-domains are also sometimes known as domains I-IV or alternatively as LI, SI, LII and SII as they extend from the amino terminus. Amino acid sequences of the receptors have been analyzed and the sequences appear to be homologous and have been aligned. Alignments of the ectodomains of ErbB1, ErbB2, ErbB3 and ErbB4 are provided in US Patent Publication No. 2006/0234343 in FIGS. 1A and 1B.

The sub-domains are composed of smaller domains known as subregions. For example, the SI or CR1 sub-domain contains 8 disulfide bonded subregions sometimes known as modules which are numbered 1-8 as they extend from the amino to carboxy terminal direction. SII contains seven (7) modules numbered 1-7. A large ordered loop has been identified in module 5 that is thought to project directly away from the ligand binding site. The amino acid sequence in this loop is highly conserved.

Chimeric ErbB ligand binding molecules are disclosed wherein sub-domains LI, SI, LII and module 1 of SII from at least two different ErbB receptors are combined in a single binding molecule. For purposes of this disclosure, the phrase "chimeric" with respect to the ErbB ligand binding molecule is intended to mean a single ErbB ligand binding molecule made from and containing portions of more than one ErbB receptor ectodomain. The phrases "ErbB chimera" and "chimeric ErbB ligand binding molecule" are used interchangeably in this application and are intended to be synonymous and refer to the protein sequence of a monomer. As can be appreciated in some embodiments the chimera molecules may dimerize through formation of disulfide bonds.

Surprisingly, it has been found that portions of the amino acid sequence of ErbB3 or ErbB4 can be combined with portions of ErbB1 through an SI linking domain to create a chimeric binding molecule that binds ligands to both of the combined receptors. Thus, the combination of ErbB1 and ErbB4 domains can be used to produce a chimeric binding molecule that has affinity for both heregulin (ErbB4 specific ligand) and TGFα (ErbB1 specific ligand).

The switch in the amino acid sequence from one receptor type to another can be at any suitable location that provides for broad spectrum and high affinity binding of ErbB ligands. In some embodiments the switch can occur in the SI sub-domain which links LI and LII sub-domains. In some embodiments the switch will occur in regions where amino acid sequences are homologous or identical between the receptors being combined, such as in module 5 of the SI sub-domain.

For purposes of this disclosure the term "homology" is intended to mean a region of amino acid sequence having identical or conservative amino acid substitutions as that term is generally understood in the art. For example with respect to an ErbB4/ErbB1 chimera, as shown in FIG. 3, a switch from the ErbB4 to the ErbB1 sequence can take place in module 5 of the SI sub-domain such that the sequence ending in VYNP from the ErbB4 sequence is followed by TTYQ from the ErbB1 sequence, as shown by the highlighted sequence in FIG. 3.

The sequence can extend as far into the ErbB1 LII domain as is required for ErbB1 ligand binding. The entire ErbB1 LII domain can be included and a portion or all of the subsequent SII region from ErbB1 can also be included. FIG. 3 shows an ectodomain amino acid alignment of the LI, SI, LII and module 1 of the SII domain of ErbB4 and ErbB1, ending at amino acid 501 of ErbB1.

With reference to FIG. 3, one chimeric ErbB embodiment is shown in which subdomain LI is derived from ErbB4; the SI region is derived from a portion of the SI region of ErbB4 and switches to a portion of the SI region of the ErbB1 in module 5. This sequence continues on to include the ErbB1 LII subdomain and module 1 of the ErbB1 SII domain. This can be designated as follows: LI (ErbB4)—SI (ErbB4/ErbB1)—LII (ErbB1)—SIIm1 (ErbB1). More specifically: LI (ErbB4 amino acids 1-245)—SI (ErbB1 starting with amino acid 249)—LII (ErbB1)—SIIm1 (ErbB1 ending with amino acid 501 according to the numbering of native ErbB1).

All of the amino acid numbering in this application is intended to be exclusive of the native signal peptide.

In certain embodiments the SI domain can be composed of portions of each of the two sub-domains, as indicated previously. Further, it is also possible to introduce substitutions into the amino acid sequence for a variety of purposes. For example, the DNA sequence for the chimeric binding molecule can be changed to remove cysteines so that the formation of aggregates through cysteine-cysteine bonds can be avoided. Substitutions of amino acids in one subdomain can be used to modify ligand binding affinities. For example, an amino acid from ErbB1 can be substituted into the ErbB4 LI subdomain to make that domain's sequence more like that of ErbB1 in order to modify the affinity of the molecule to ErbB ligands. Similarly, amino acid substitutions from ErbB3 or 4 LII subdomains can be included into the ErbB1 subdomain. Such substitutions can also be made in the SI and SII subdomains. Although any number of such substitutions can be considered substitutions of glutamine from ErbB1 for serine in the ErbB4 portion at position 13, tyrosine for serine at position 42, arginine for tyrosine at position 123 are representative examples. Other examples can be identified by one of skill in the art simply by comparing sequences. Substitutions that are not homologous can also be considered. For example, asparagine could be substituted for serine at position 13 rather than the glutamine found in ErbB1 or a residue that has intermediate characteristics of the residues found in both receptors may be used.

Any of these chimeric molecules could also be fused to other molecules or portions thereof including: other chimeric receptors (of any growth factor receptor family) or to sequences that facilitate purification of the product. The DNA sequences can be obtained from commercial sources and placed in any suitable expression vector and expressed from suitable hosts of which many are known.

In one embodiment the ErbB chimera can be fused with components that cause aggregative conjugate formation or extend protein half-life. For example, the ErbB chimera can be fused to the constant region of immunoglobulin molecule such as the Fc region of IgG. For purposes of this disclosure one suitable Fc region is known as IgG2Fc, although others are also known in the art and can be used.

For purposes of this application suitable binding affinities are affinities that are high enough to bind ErbB ligands in a physiological matrix. Preferably, dissociation constants will be no higher than about 10-fold to about 100-fold above the dissociation constants of the native receptors. More preferably, the dissociation constants for the ErbB chimera will be within 10-fold of their native receptor counterparts and more preferably within the same order of magnitude. Most preferably the binding affinities of the chimeric molecules will not be distinguishable from the native-counterparts. Any affinity that is sufficient to bind and sequester ErbB ligands to thereby prevent or interfere with ligand binding and activating ErbB receptors is suitable for use and can find use in the disclosed methods. Binding affinity, which is a proxy for inhibitor potency, of the binding molecules can be measured using biosensor technology or by classic binding assays such as ELISA which are well known in the art.

DNA that encodes the chimeric ErbB ligand binding molecule sequences is also contemplated. One of skill can appreciate that the genetic code can be used to prepare suitable DNA sequences and codon preferences for specific expression hosts can also be incorporated into such sequences. Also contemplated for use with these sequences are additional DNA sequences that can be used for the expression of these DNA sequences. A variety of these are known. As is well known in the art such sequences can also be introduced into host cells for the maintenance of the DNA and for its expression and such hosts that include these DNA sequences are also contemplated.

Pharmaceutical compositions comprising a disclosed chimeric ErbB ligand binding molecule are also contemplated. Such compositions comprise a therapeutically effective amount of a chimeric ErbB ligand binding molecule, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle in which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like in which the chimeric ErbB ligand binding molecule is soluble and is chemically stable. The composition can also contain wetting or emulsifying agents, or pH buffering agents. These compositions can take the form of solutions, suspensions, emulsion, tablets, pills, capsules, powders, sustained-release formulations and the like. Pharmaceutically acceptable carriers include other ingredients for use in formulations such as DPPC, DOPE, DSPC and DOPC. Natural or synthetic surfactants may be used. PEG may be used (even apart from its use in derivatizing the protein or analog). Dextrans, such as cyclodextran, may be used. Cellulose and cellulose derivatives may be used. Amino acids may be used, such as use in a buffered formulation. Pharmaceutically acceptable diluents include buffers having various contents (e.g., Tris-HCl, acetate, phosphate), pH and ionic strength; additives such as detergents and solubilizing agents (e.g., Polysorbate 80), antioxidants (e.g., ascorbic acid, sodium metabisulfite), preservatives (e.g., benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations. Liposome, microcapsule or microsphere, inclusion complexes, or other types of carriers are also contemplated.

The amount of the active chimeric binding molecule that will be effective for its intended therapeutic use can be determined by standard clinical techniques. In addition, in vitro assays may optionally be employed to help identify optimal dosage ranges. Generally, the daily regimen should be in the range of 0.1-1000 micrograms of the active agent (API) kilogram of body weight, preferably 0.1-150 micrograms per kilogram. Effective doses may be extrapolated from dose-response curves derived from in vitro or suitable animal model test systems. Dosage amount and interval may be adjusted individually to provide plasma levels of the compounds that are sufficient to maintain therapeutic effect. In cases of local administration or selective uptake, the effective local concentration of the compounds may not be related to plasma concentration. The dosage regimen involved in a method for treatment can be determined by the attending physician, considering various factors which modify the action of drugs, e.g. the age, condition, body weight, sex and diet of the patient, the severity of disease, time of administration and other clinical factors.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

A method for treating a patient in need of treatment is disclosed that includes obtaining a chimeric ErbB ligand binding molecule that binds ErbB ligands and interferes with the interaction and effect of ligands on the ErbB receptor system of cancer cells, and administering a therapeutically effective amount of the molecule to a patient. Administration can be by parenteral routes such as i.v. administration, direct injection into a solid tumor such as through a syringe or catheter or by i.p. injection.

In one method of treatment the chimeric ErbB ligand binding molecules can be immobilized to a solid support such as an apheresis or biocore support by standard methods. When the binding molecule is immobilized to a solid support the serum, blood or other biologically relevant fluid of a patient can be placed in contact with the solid support in the apheresis column to remove ErbB ligands from the fluid. The serum, blood or fluid can then be reintroduced into the patient.

The binding molecules can also be used in combination therapies. Thus, the chimeric ErbB ligand binding molecule may be administered in combination with one or more additional compounds or therapies, including chemotherapeutic agents, surgery, catheter devices, and radiation. Combination therapy includes administration of a single pharmaceutical dosage formulation which contains a chimeric ErbB ligand binding molecule and one or more additional agents. The chimeric ErbB ligand binding molecule and one or more additional agent(s) can be administered in their own separate pharmaceutical dosage formulations or together in the same formulation. For example, a chimeric ErbB ligand binding molecule and a cytotoxic agent, a chemotherapeutic agent or a growth inhibitory agent can be administered to the patient together in a single dosage composition or each agent can be administered in a separate dosage formulation. More specifically, the chimeric ErbB ligand binding molecule can be used in combination therapies that include therapeutic agents such as Lapatinib®, Herceptin®, Erbitux® and the like. Where separate dosage formulations are used, the chimeric ErbB ligand binding molecules and one or more additional agents can be administered concurrently, or at separately staggered times, i.e., sequentially. One of skill in the art can appreciate that the combination must be such that the chimeric ErbB ligand binding molecule does not interfere, but rather, accentuates the second therapeutic in the combination.

The following examples are given by way of illustration only and in no way should be construed as limiting the subject matter of the present application. In the following examples, nucleotide sequences that encode the disclosed amino acid sequences are also contemplated. Many of the following examples disclose the sequence for IgG2Fc fused to the ErbB chimera. It should be appreciated that use of IgGFc is optional. In addition, the conservative replacement of an amino acid with another similar amino acid that does not substantially (about 10-fold) interfere with ligand binding activity is specifically contemplated. Conventional binding studies of the purified products can be used to determine whether substantial differences in binding affinities exist. Many of the structures described below can be better understood by reference to the diagrams of those structures in FIGS. 1 and 2. All sequences include a signal peptide derived from a mouse antibody heavy chain gene. All numbering is exclusive of the signal peptide, and the first amino acid of each ErbB sequence is underlined.

EXAMPLE 1

The present example specifically discloses a chimera containing a signal peptide (M E W S W V F L F F L S V T T G V H S) joined to the LI subdomain of the ErbB3 receptor and the SI and LII subdomains of the ErbB1 receptor terminating after residue 501 in module 1 of the ErbB1 SII sub-domain. The ErbB chimera has the following amino acid sequence.

SEQ. ID. NO. 1

```
M E W S W V F L F F L S V T T G V H S S E V G N S Q A V C P G T L N G L S V T G D
A E N Q Y Q T L Y K L Y E R C E V V M G N L E I V L T G H N A D L S F L Q W I R E
V T G Y V L V A M N E F S T L P L P N L R V V R G T Q V Y D G K F A I F V M L N Y
N T N S S H A L R Q L R L T Q L T E I L S G G V Y I E K N D K L C H M D T I D W R
D I V R D R D A E I V V K D N G R S C P P C D P S C P N G S C W G A G E E N C Q K
L T K I I C A Q Q C S G R C R G K S P S D C C H N Q C A A G C T G P R E S D C L V C
R K F R D E A T C K D T C P P L M L Y N P T T Y Q M D V N P E G K Y S F G A T C V
K K C P R N Y V V T D H G S C V R A C G A D S Y E M E E D G V R K C K K C E G P
C R K V C N G I G I G E F K D S L S I N A T N I K H F K N C T S I S G D L H I L P V A
F R G D S F T H T P P L D P Q E L D I L K T V K E I T G F L L I Q A W P E N R T D L H
A F E N L E I I R G R T K Q H G Q F S L A V V S L N I T S L G L R S L K E I S D G D V
I I S G N K N L C Y A N T I N W K K L F G T S G Q K T K I I S N R G E N S C K A T G
Q V C H A L C S P E G C W G P E P R D C V S V E C P P C P A P P V A G P S V F L F P
```

```
PKPKDTLMISRTPEVTCVVVDVSHEDPEVQFNWYVDGMEVH

NAKTKPREEQFNSTFRVVSVLTVVHQDWLNGKEYKCKVSN

KGLPAPIEKTISKTKGQPREPQVYTLPPSREEMTKNQVSLTC

LVKGFYPSDIAVEWESNGQPENNYKTTPPMLDSDGSFFLYS

KLTVDKSRWQQGNVFSCSVMHEALHNHYTQKSLSLSPGK
Stop
```

EXAMPLE 2

The present example specifically discloses a chimera containing a signal peptide (M E W S W V F L F F L S V T T G V H S) joined to LI and SI subdomains of ErbB3 receptor and the LII subdomain of the ErbB1 receptor terminating after residue 501 in module 1 of the ErbB1 SII sub-domain. The ErbB chimera has the following amino acid sequence:

```
                                                         SEQ. ID. NO. 2
MEWSWVFLFFLSVTTGVHSSEVGNSQAVCPGTLNGLSVTGD

AENQYQTLYKLYERCEVVMGNLEIVLTGHNADLSFLQWIRE

VTGYVLVAMNEFSTLPLPNLRVVRGTQVYDGKFAIFVMLNY

NTNSSHALRQLRLTQLTEILSGGVYIEKNDKLCHMDTIDWR

DIVRDRDAEIVVKDNGRSCPPCHEVCKGRCWGPGSEDCQTL

TKTICAPQCNGHCFGPNPNQCCHDECAGGCSGPQDTDCFAC

RHFNDSGACVPRCPQPLVYNKLTFQLEPNPHTKYQYGGVCV

ASCPHNFVVDQTSCVRACPPDKMEVDKNGLKMCEPCGGLC

PKVCNGIGIGEFKDSLSINATNIKHFKNCTSISGDLHILPVAF

RGDSFTHTPPLDPQELDILKTVKEITGFLLIQAWPENRTDLH

AFENLEIIRGRTKQHGQFSLAVVSLNITSLGLRSLKEISDGDV

IISGNKNLCYANTINWKKLFGTSGQKTKIISNRGENSCKATG

QVCHALCSPEGCWGPEPRDCVSVECPPCPAPPVAGPSVFLFP

PKPKDTLMISRTPEVTCVVVDVSHEDPEVQFNWYVDGMEVH

NAKTKPREEQFNSTFRVVSVLTVVHQDWLNGKEYKCKVSN

KGLPAPIEKTISKTKGQPREPQVYTLPPSREEMTKNQVSLTC

LVKGFYPSDIAVEWESNGQPENNYKTTPPMLDSDGSFFLYS

KLTVDKSRWQQGNVFSCSVMHEALHNHYTQKSLSLSPGK
Stop
```

EXAMPLE 3

The present example discloses a chimera containing a signal peptide (M E W S WV F L F F L S V T T G V H S) joined to the LI subdomain and modules 1-2 of the SI subdomain of the ErbB3 receptor and modules 3-8 of the SI subdomain, the LII subdomain and module 1 of SII subdomain of the ErbB1 receptor fused to IgG2Fc. The ErbB chimera has the following amino acid sequence:

```
                                                         SEQ. ID. NO. 3
MEWSWVFLFFLSVTTGVHSSEVGNSQAVCPGTLNGLSVTGD

AENQYQTLYKLYERCEVVMGNLEIVLTGHNADLSFLQWIRE

VTGYVLVAMNEFSTLPLPNLRVVRGTQVYDGKFAIFVMLNY

NTNSSHALRQLRLTQLTEILSGGVYIEKNDKLCHMDTIDWR
```

-continued

```
D I V R D R D A E I V V K D N G R S C P P C H E V C K G R C W G P G S E D C Q T L
T K T I C A P Q C N G H C F G P N P N Q C C H N Q C A A G C T G P R E S D C L V C
R K F R D E A T C K D T C P P L M L Y N P T T Y Q M D V N P E G K Y S F G A T C V
K K C P R N Y V V T D H G S C V R A C G A D S Y E M E E D G V R K C K K C E G P
C R K V C N G I G I G E F K D S L S I N A T N I K H F K N C T S I S G D L H I L P V A
F R G D S F T H T P P L D P Q E L D I L K T V K E I T G F L L I Q A W P E N R T D L H
A F E N L E I I R G R T K Q H G Q F S L A V V S L N I T S L G L R S L K E I S D G D V
I I S G N K N L C Y A N T I N W K K L F G T S G Q K T K I I S N R G E N S C K A T G
Q V C H A L C S P E G C W G P E P R D C V S V E C P P C P A P P V A G P S V F L F P
P K P K D T L M I S R T P E V T C V V V D V S H E D P E V Q F N W Y V D G M E V H
N A K T K P R E E Q F N S T F R V V S V L T V V H Q D W L N G K E Y K C K V S N
K G L P A P I E K T I S K T K G Q P R E P Q V Y T L P P S R E E M T K N Q V S L T C
L V K G F Y P S D I A V E W E S N G Q P E N N Y K T T P P M L D S D G S F F L Y S
K L T V D K S R W Q Q G N V F S C S V M H E A L H N H Y T Q K S L S L S P G K
Stop
```

EXAMPLE 4

The present example discloses a chimera containing a signal peptide (M E W S W V F L F F L S V T T G V H S) joined to the LI subdomain and modules 1-3 of the SI subdomain of ErbB3 receptor and modules 4-8 of the SI subdomain, the LII subdomain and module 1 of SII subdomain of the ErbB1 receptor fused to IgG2Fc. The ErbB chimera has the following amino acid sequence:

SEQ. ID. NO. 4
```
M E W S W V F L F F L S V T T G V H S S E V G N S Q A V C P G T L N G L S V T G D
A E N Q Y Q T L Y K L Y E R C E V V M G N L E I V L T G H N A D L S F L Q W I R E
V T G Y V L V A M N E F S T L P L P N L R V V R G T Q V Y D G K F A I F V M L N Y
N T N S S H A L R Q L R L T Q L T E I L S G G V Y I E K N D K L C H M D T I D W R
D I V R D R D A E I V V K D N G R S C P P C H E V C K G R C W G P G S E D C Q T L
T K T I C A P Q C N G H C F G P N P N Q C C H D E C A G G C S G P Q D T D C F V C
R K F R D E A T C K D T C P P L M L Y N P T T Y Q M D V N P E G K Y S F G A T C V
K K C P R N Y V V T D H G S C V R A C G A D S Y E W E E D G V R K C K K C E G P
C R K V C N G I G I G E F K D S L S I N A T N I K H F K N C T S I S G D L H I L P V A
F R G D S F T H T P P L D P Q E L D I L K T V K E I T G F L L I Q A W P E N R T D L H
A F E N L E I I R G R T K Q H G Q F S L A V V S L N I T S L G L R S L K E I S D G D V
I I S G N K N L C Y A N T I N W K K L F G T S G Q K T K I I S N R G E N S C K A T G
Q V C H A L C S P E G C W G P E P R D C V S V E C P P C P A P P V A G P S V F L F P
P K P K D T L M I S R T P E V T C V V V D V S H E D P E V Q F N W Y V D G M E V H
N A K T K P R E E Q F N S T F R V V S V L T V V H Q D W L N G K E Y K C K V S N
K G L P A P I E K T I S K T K G Q P R E P Q V Y T L P P S R E E M T K N Q V S L T C
L V K G F Y P S D I A V E W E S N G Q P E N N Y K T T P P M L D S D G S F F L Y S
K L T V D K S R W Q Q G N V F S C S V M H E A L H N H Y T Q K S L S L S P G K
Stop
```

EXAMPLE 5

The present example specifically discloses a chimera containing a signal peptide (M E W S W V F L F F L S V T T G V H S) joined to the LI subdomain and modules 1-4 of the SI subdomain of ErbB3 receptor with modules 5-8 of the SI subdomain, the LII subdomain and module 1 of SII subdomain of the ErbB1 receptor fused to IgG2Fc. The ErbB chimera has the following amino acid sequence:

```
                                                          SEQ. ID. NO. 5
M E W S W V F L F F L S V T T G V H S S E V G N S Q A V C P G T L N G L S V T G D
A E N Q Y Q T L Y K L Y E R C E V V M G N L E I V L T G H N A D L S F L Q W I R E
V T G Y V L V A M N E F S T L P L P N L R V V R G T Q V Y D G K F A I F V M L N Y
N T N S S H A L R Q L R L T Q L T E I L S G G V Y I E K N D K L C H M D T I D W R
D I V R D R D A E I V V K D N G R S C P P C H E V C K G R C W G P G S E D C Q T L
T K T I C A P Q C N G H C F G P N P N Q C C H D E C A G G C S G P Q D T D C F A C
R H F N D S G A C V P T C P P L M L Y N P T T Y Q M D V N P E G K Y S F G A T C V
K K C P R N Y V V T D H G S C V R A C G A D S Y E M E E D G V R K C K K C E G P
C R K V C N G I G I G E F K D S L S I N A T N I K H F K N C T S I S G D L H I L P V A
F R G D S F T H T P P L D P Q E L D I L K T V K E I T G F L L I Q A W P E N R T D L H
A F E N L E I I R G R T K Q H G Q F S L A V V S L N I T S L G L R S L K E I S D G D V
I I S G N K N L C Y A N T I N W K K L F G T S G Q K T K I I S N R G E N S C K A T G
Q V C H A L C S P E G C W G P E P R D C V S V E C P P C P A P P V A G P S V F L F P
P K P K D T L M I S R T P E V T C V V V D V S H E D P E V Q F N W Y V D G M E V H
N A K T K P R E E Q F N S T F R V V S V L T V V H Q D W L N G K E Y K C K V S N
K G L P A P I E K T I S K T K G Q P R E P Q V Y T L P P S R E E M T K N Q V S L T C
L V K G F Y P S D I A V E W E S N G Q P E N N Y K T T P P M L D S D G S F F L Y S
K L T V D K S R W Q Q G N V F S C S V M H E A L H N H Y T Q K S L S L S P G K
Stop
```

EXAMPLE 6

The present example specifically discloses a chimera containing a signal peptide (M E W S W V F L F F L S V T T G V H S) joined to the LI subdomain and modules 1-5 of the SI subdomain of ErbB3 receptor with the modules 6-8 of the SI subdomain, the LII subdomain and module 1 of the SII subdomain of the ErbB1 receptor fused to IgG2Fc. The ErbB chimera has the following amino acid sequence:

```
                                                          SEQ. ID. NO. 6
M E W S W V F L F F L S V T T G V H S S E V G N S Q A V C P G T L N G L S V T G D
A E N Q Y Q T L Y K L Y E R C E V V M G N L E I V L T G H N A D L S F L Q W I R E
V T G Y V L V A M N E F S T L P L P N L R V V R G T Q V Y D G K F A I F V M L N Y
N T N S S H A L R Q L R L T Q L T E I L S G G V Y I E K N D K L C H M D T I D W R
D I V R D R D A E I V V K D N G R S C P P C H E V C K G R C W G P G S E D C Q T L
T K T I C A P Q C N G H C F G P N P N Q C C H D E C A G G C S G P Q D T D C F A C
R H F N D S G A C V P R C P Q P L V Y N K L T F Q L E P N P H T K Y Q Y G G V C V
A K C P R N Y V V T D H G S C V R A C G A D S Y E M E E D G V R K C K K C E G P
C R K V C N G I G I G E F K D S L S I N A T N I K H F K N C T S I S G D L H I L P V A
F R G D S F T H T P P L D P Q E L D I L K T V K E I T G F L L I Q A W P E N R T D L H
A F E N L E I I R G R T K Q H G F S L A V V S L N I T S L G L R S L K E I S D G D V
```

-continued
```
I I S G N K N L C Y A N T I N W K K L F G T S G Q K T K I I S N R G E N S C K A T G Q V C H A L C S P E G C W G P E P R D C V S V E C P P C P A P P V A G P S V F L F P P K P K D T L M I S R T P E V T C V V V D V S H E D P E V Q F N W Y V D G M E V H

N A K T K P R E E Q F N S T F R V V S V L T V V R Q D W L N G K E Y K C K V S N

K G L P A P I E K T I S K T K G Q P R E P Q V Y T L P P S R E E M T K N Q V S L T C

L V K G F Y P S D I A V E W E S N G Q P E N N Y K T T P P M L D S D G S F F L Y S

K L T V D K S R W Q Q G N V F S C S V M H E A L H N H Y T Q K S L S L S P G K
Stop
```

EXAMPLE 7

The present example describes a chimera containing a signal peptide (M E W S W V F L F F L S V T T G V H S) joined to the LI subdomain and modules 1-6 of the SI subdomain of the ErbB3 receptor with the modules 7-8 of the SI subdomain, the LII subdomain and module 1 of the SII subdomain of the ErbB1 receptor fused to IgG2Fc. The ErbB chimera has the following amino acid sequence:

```
                                                              SEQ. ID. NO. 7
M E W S W V F L F F L S V T T G V H S S E V G N S Q A V C P G T L N G L S V T G D

A E N Q Y Q T L Y K L Y E R C E V V M G N L E I V L T G H N A D L S F L Q W I R E

V T G Y V L V A M N E F S T L P L P N L R V V R G T Q V Y D G K F A I F V M L N Y

N T N S S H A L R Q L R L T Q L T E I L S G G V Y I E K N D K L C H M D T I D W R

D I V R D R D A E I V V K D N G R S C P P C H E V C K G R C W G P G S E D C Q T L

T K T I C A P Q C N G H C F G P N P N Q C C H D E C A G G C S G P Q D T D C F A C

R H F N D S G A C V P R C P Q P L V Y N K L T F Q L E P N P H T K Y Q Y G G V C V

A S C P H N F V V D Q T S C V R A C G A D S Y E M E E D G V R K C K K C E G P C

R K V C N G I G I G E F K D S L S I N A T N I K H F K N C T S I S G D L H I L P V A F

R G D S F T H T P P L D P Q E L D I L K T V K E I T G F L L I Q A W P E N R T D L H

A F E N L E I I R G R T K Q H G Q F S L A V V S L N I T S L G L R S L K E I S D G D V

I I S G N K N L C Y A N T I N W K K L F G T S G Q K T K I I S N R G E N S C K A T G

Q V C H A L C S P E G C W G P E P R D C V S V E C P P C P A P P V A G P S V F L F P

P K P K D T L M I S R T P E V T C V V V D V S H E D P E V Q F N W Y V D G M E V H

N A K T K P R E E Q F N S T F R V V S V L T V V H Q D W L N G K E Y K C K V S N

K G L P A P I E K T I S K T K G Q P R E P Q V Y T L P P S R E E M T K N Q V S L T C

L V K G F Y P S D I A V E W E S N G Q P E N N Y K T T P P M L D S D G S F F L Y S

K L T V D K S R W Q Q G N V F S C S V M H E A L H N H Y T Q K S L S L S P G K
Stop
```

EXAMPLE 8

The present example discloses a chimera containing a signal peptide (M E W S W V F L F F L S V T T G V H S) joined to the LI subdomain and modules 1-7 of the SI subdomain of the ErbB3 receptor and module 8 of the SI subdomain, the LII subdomain and module 1 of the SII subdomain of the ErbB1 receptor fused to IgG2Fc. The ErbB chimera has the following amino acid sequence:

```
                                                              SEQ. ID. NO. 8
M E W S W V F L F F L S V T T G V H S S E V G N S Q A V C P G T L N G L S V T G D

A E N Q Y Q T L Y K L Y E R C E V V M G N L E I V L T G H N A D L S F L Q W I R E
```

-continued

```
VTGYVLVAMNEFSTLPLPNLRVVRGTQVYDGKFAIFVMLNY
NTNSSHALRQLRLTQLTEILSGGVYIEKNDKLCHMDTIDWR
DIVRDRDAEIVVKDNGRSCPPCHEVCKGRCWGPGSEDCQTL
TKTICAPQCNGHCFGPNPNQCCHDECAGGCSGPQDTDCFAC
RHFNDSGACVPRCPQPLVYNKLTFQLEPNPHTKYQYGGVCV
ASCPHNFVVDQTSCVRACPPDKMEVDKNGLKMCEPCEGPCR
KVCNGIGIGEFKDSLSINATNIKHFKNCTSISGDLHILPVAFR
GDSFTHTPPLDPQELDILKTVKEITGFLLIQAWPENRTDLHA
FENLEIIRGRTKQHGQFSLAVVSLNITSLGLRSLKEISDGDVI
ISGNKNLCYANTINWKKLFGTSGQKTKIISNRGENSCKATGQ
VCHALCSPEGCWGPEPRDCVSVECPPCPAPPVAGPSVFLFPP
KPKDTLMISRTPEVTCVVVDVSHEDPEVQFNWYVDGMEVH
NAKTKPREEQFNSTFRVVSVLTVVHQDWLNGKEYKCKVSN
KGLPAPIEKTISKTKGQREPQVYTLPPSREEMTKNQVSLTC
LVKGFYPSDIAVEWESNGQPENNYKTTPPMLDSDGSFFLYS
KLTVDKSRWQQGNVFSCSVMHEALHNHYTQKSLSLSPGK
Stop
```

EXAMPLE 9

The present example discloses a chimera containing a signal peptide (M E W S W V F L F F L S V T T G V H S) joined to the LI subdomain and module 1 of the SI subdomain of the ErbB3 receptor and modules 2-8 of the SI subdomain, the LII subdomain and module 1 of the SII subdomain of the ErbB1 receptor fused to IgG2Fc. The ErbB chimera has the following amino acid sequence:

SEQ. ID. NO. 9
```
MEWSWVFLFFLSVTTGVHSSEVGNSQAVCPGTLNGLSVTGD
AENQYQTLYKLYERCEVVMGNLEIVLTGHNADLSFLQWIRE
VTGYVLVAMNEFSTLPLPNLRVVRGTQVYDGKFAIFVMLNY
NTNSSHALRQLRLTQLTEILSGGVYIEKNDKLCHMDTIDWR
DIVRDRDAEIVVKDNGRSCPPCHEVCKGRCWGPGSEDCQTL
TKIICAQQCSGRCRGKSPSDCCHNQCAAGCTGPRESDCLVC
RKFRDEATCKDTCPPLMLYNPTTYQMDVNPEGKYSFGATCV
KKCPRNYVVTDHGSCVRACGADSYEMEEDGVRKCKKCEGP
CRKVCNGIGIGEFKDSLSINATNIKHFKNCTSISGDLHILPVA
FRGDSFTHTPPLDPQELDILKTVKEITGFLLIQAWPENRTDLH
AFENLEIIRGRTKQHGQFSLAVVSLNITSLGLRSLKEISDGDV
IISGNKNLCYANTINWKKLFGTSGQKTKIISNRGENSCKATG
QVCHALCSPEGCWGPEPRDCVSVECPPCPAPPVAGPSVFLFP
PKPKDTLMISRTPEVTCVVVDVSHEDPEVQFNWYVDGMEVH
NAKTKPREEQFNSTFRVVSVLTVVHQDWLNGKEYKCKVSN
KGLPAPIEKTISKTKGQREPQVYTLPPSREEMTKNQVSLTC
LVKGFYPSDIAVEWESNGQPENNYKTTPPMLDSDGSFFLYS
KLTVDKSRWQQGNVFSCSVMHEALHNHYTQKSLSLSPGK
Stop
```

EXAMPLE 10

The present example discloses a chimera containing a signal peptide (M E W S W V F L F F L S V T T G V H S) joined to the LI subdomain of the ErbB4 receptor and the SI subdomain, the LII subdomain and module 1 of the SII subdomain of the ErbB1 receptor fused to IgG2Fc. The ErbB chimera has the following amino acid sequence:

SEQ. ID. NO. 10
M E W S W V F L F F L S V T T G V H S Q S V C A G
T E N K L S S L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C D P S C P N G S C W G A G E E N C
Q K L T K I I C A Q Q C S G R C R G K S P S D C C
H N Q C A A G C T G P R E S D C L V C R K F R D E
A T C K D T C P P L M L Y N P T T Y Q M D V N P E
G K Y S F G A T C V K K C P R N Y V V T D H G S C
V R A C G A D S Y E M E E D G V R K C K K C E G P
C R K V C N G I G I E F K D S L S I N A T N I K
H F K N C T S I S G D L H I L P V A F R G D S F T
H T P P L D P Q E L D I L K T V K E I T G F L L I
Q A W P E N R T D L H A F E N L E I I R G R T K Q
H G Q F S L A V V S L N I T S L G L R S L K E I S
D G D V I I S G N K N L C Y A N T I N W K K L F G
T S G Q K T K I I S N R G E N S C K A T G Q V C H
A L C S P E G C W G P E P R D C V S V E C P P C P
A P P V A G P S V F L F P P K P K D T L M I S R T
P E V T C V V V D V S H E D P E V Q F N W Y V D G
M E V H N A K T K P R E E Q F N S T F R V V S V L
T V V H Q D W L N G K E Y K C K V S N K G L P A P
I E K T I S K T K G Q P R E P Q V Y T L P P S R E
E M T K N Q V S L T C L V K G F Y P S D I A V E W
E S N G Q P E N N Y K T T P P M L D S D G S F F L
Y S K L T V D K S R W Q Q G N V F S C S V M H E A
L H N H Y T Q K S L S L S P G K Stop

EXAMPLE 11

The present example discloses a chimera containing a signal peptide (M E W S W V F L F F L S V T T G V H S) joined to the LI subdomain and the SI subdomain of the ErbB4 receptor and LII subdomain and module 1 of the SII subdomain of the ErbB1 receptor fused to IgG2Fc. The ErbB chimera has the following amino acid sequence:

SEQ. ID. NO. 11
M E W S W V F L F F L S V T T G V H S Q S V C A G
T E N K L S S L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C H K S C T G R C W G P T E N H C Q
T L T R T V C A E Q C D G R C Y G P Y V S D C C H
R E C A G G C S G P K D T D C F A C M N F N D S G
A C V T Q C P Q T F V Y N P T T F Q L E H N F N A
K Y T Y G A F C V K K C P H N F V V D S S S C V R
A C P S S K M E V E E N G I K M C K P C T D I C P
K V C N G I G I G E F K D S L S I N A T N I K H F
K N C T S I S G D L H I L P V A F R G D S F T H T
P P L D P Q E L D I L K T V K E I T G F L L I Q A
W P E N R T D L H A F E N L E I I R G R T K Q H G
Q F S L A V V S L N I T S L G L R S L K E I S D G
D V I I S G N K N L C Y A N T I N W K K L F G T S
G Q K T K I I S N R G E N S C K A T G Q V C H A L
C S P E G C W G P E P R D C V S V E C P P C P A P
P V A G P S V F L F P P K P K D T L M I S R T P E
V T C V V V D V S H E D P E V Q F N W Y V D G M E
V H N A K T K P R E E Q F N S T F R V V S V L T V
V H Q D W L N G K E Y K C K V S N K G L P A P I E
K T I S K T K G Q P R E P Q V Y T L P P S R E E M
T K N Q V S L T C L V K G F Y P S D I A V E W E S
N G Q P E N N Y K T T P P M L D S D G S F F L Y S
K L T V D K S R W Q Q G N V F S C S V M H E A L H
N H Y T Q K S L S L S P G K Stop

EXAMPLE 12

The present example refers to a chimera containing a signal peptide (M E W S W V F L F F L S V T T G V H S) joined to the LI subdomain and the modules 1-2 of the SI subdomain of the ErbB4 receptor and the modules 3-8 of the SI subdomain, the LII subdomain and module 1 of the SII subdomain of the ErbB1 receptor fused to IgG2Fc. The ErbB chimera has the following amino acid sequence:

SEQ. ID. NO. 12
M E W S W V F L F F L S V T T G V H S Q S V C A G
T E N K L S S L S D L E Q Q Y R A L R K Y Y E N C

-continued

```
E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T R T V C A E Q C D G R C Y G P Y V S D C C H

N Q C A A G C T G P R E S D C L V C R K F R D E A

T C K D T C P P L M L Y N P T T Y Q M D V N P E G

K Y S F G A T C V K K C P R N Y V V T D H G S C V

R A C G A D S Y E M E E D G V R K C K K C E G P C

R K V C N G I G I G E F K D S L S I N A T N I K H

F K N C T S I S G D L H I L P V A F R G D S F T H

T P P L D P Q E L D I L K T V K E I T G F L L I Q

A W P E N R T D L H A F E N L E I I R G R T K Q H

G Q F S L A V V S L N I T S L G L R S L K E I S D

G D V I I S G N K N L C Y A N T I N W K K L F G T

S G Q K T K I I S N R G E N S C K A T G Q V C H A

L C S P E G C W G P E P R D C V S V E C P P C P A

P P V A G P S V F L F P P K P K D T L M I S R T P

E V T C V V V D V S H E D P E V Q F N W Y V D G M

E V H N A K T K P R E E Q F N S T F R V V S V L T

V V H Q D W L N G K E Y K C K V S N K G L P A P I

E K T I S K T G Q P R E P Q V Y T L P P S R E E

M T K N Q V S L T C L V K G F Y P S D I A V E W E

S N G Q P E N N Y K T T P P M L D S D G S F F L Y

S K L T V D K S R W Q Q G N V F S G S V M H E A L

H N H Y T Q K S L S L S P G K Stop
```

EXAMPLE 13

The present example refers to a chimera containing a signal peptide (M E W S W V F L F F L S V T T G V H S) joined to the LI subdomain and the modules 1-3 of the SI subdomain of the ErbB4 receptor and the modules 4-8 of the SI subdomain, the LII subdomain and module 1 of the SII subdomain of the ErbB1 receptor fused to IgG2Fc. The ErbB chimera has the following amino acid sequence:

```
                                    SEQ. ID. NO. 13
M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T R T V C A E Q C D G R C Y G P Y V S D C C H

R E C A G G C S G P K D T D C F V C R K F R D E A

T C K D T C P P L M L Y N P T T Y Q M D V N P E G

K Y S F G A T C V K K C P R N Y V V T D H G S C V

R A C G A D S Y E M E E D G V R K C K K C E G P C

R K V C N G I G I G E F K D S L S I N A T N I K H

F K N C T S I S G D L H I L P V A F R G D S F T H

T P P L D P Q E L D I L K T V K E I T G F L L I Q

A W P E N R T D L H A F E N L E I I R G R T K Q H

G Q F S L A V V S L N I T S L G L R S L K E I S D

G D V I I S G N K N L C Y A N T I N W K K L F G T

S G Q K T K I I S N R G E N S C K A T G Q V C H A

L C S P E G C W G P E P R D C V S V E C P P C P A

P P V A G P S V F L F P P K P K D T L M I S R T P

E V T C V V V D V S H E D P E V Q F N W Y V D G M

E V H N A K T K P R E E Q F N S T F R V V S V L T

V V H Q D W L N G K E Y K C K V S N K G L P A P I

E K T I S K T G Q P R E P Q V Y T L P P S R E E

M T K N Q V S L T C L V K G F Y P S D I A V E W E

S N G Q P E N N Y K T T P P M L D S D G S F F L Y

S K L T V D K S R W Q Q G N V F S C S V M H E A L

H N H Y T Q K S L S L S P G K Stop
```

EXAMPLE 14

The present example discloses a chimera containing a signal peptide (M E W S W V F L F F L S V T T G V H S) joined to the LI subdomain and the modules 1-4 of the SI subdomain of the ErbB4 receptor and the modules 5-8 of the SI subdomain, the LII subdomain and module 1 of the SII subdomain of the ErbB1 receptor fused to IgG2Fc. The ErbB chimera has the following amino acid sequence:

```
                                    SEQ. ID. NO. 14
M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N
```

-continued

```
G S S G C G R C H K S C T G R C W G P T E N H C Q
T L T R T V C A E Q C D G R C Y G P Y V S D C C H
R E C A G G C S G P K D T D C F A C M N F N D S G
A C V T T C P P L M L Y N P T T Y Q M D V N P E G
K Y S F G A T C V K K C P R N Y V V T D H G S C V
R A C G A D S Y E M E E D G V R K C K K C E G P C
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E C P P C P A
P P V A G P S V F L F P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop
```

EXAMPLE 15

The present example discloses a chimera containing a signal peptide (M E W S W V F L F F L S V T T G V H S) joined to the LI subdomain and the modules 1-5 of the SI subdomain of the ErbB4 receptor and the modules 6-8 of the SI subdomain, the LII subdomain and module 1 of the SII subdomain of the ErbB1 receptor fused to IgG2Fc. The ErbB chimera has the following amino acid sequence:

```
                                    SEQ. ID. NO. 15
M E W S W V F L F F L S V T T G V H S Q S V C A G
T E N K L S S L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C H K S C T G R C W G P T E N H C Q
T L T R T V C A E Q C D G R C Y G P Y V S D C C H
R E C A G G C S G P K D T D C F A C M N F N D S G
A C V T Q C P Q T F V Y N P T T F Q L E H N F N A
K Y T Y G A F C V K K C P R N Y V V T D H G S C V
R A C G A D S Y E M E E D G V R K C K K C E G P C
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E C P P C P A
P P V A G P S V F L F P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop
```

EXAMPLE 16

The present example refers to a chimera containing a signal peptide (M E W S W V F L F F L S V T T G V H S) joined to the LI subdomain and the modules 1-6 of the SI subdomain of the ErbB4 receptor and the modules 7-8 of the SI subdomain, the LII subdomain and module 1 of the SI subdomain of the ErbB1 receptor fused to IgG2Fc. The ErbB chimera has the following amino acid sequence:

```
                                    SEQ. ID. NO. 16
M E W S W V F L F F L S V T T G V H S Q S V C A G
T E N K L S S L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C H K S C T G R C W G P T E N H C Q
T L T R T V C A E Q C D G R C Y G P Y V S D C C H
R E C A G G C S G P K D T D C F A C M N F N D S G
A C V T Q C P Q T F V Y N P T T F Q L E H N F N A
K Y T Y G A F C V K K C P H N F V V D S S S C V R
```

-continued

A C G A D S Y E M E E D G V R K C K K C E G P C R

K V C N G I G I G E F K D S L S I N A T N I K H F

K N C T S I S G D L H I L P V A F R G D S F T H T

P P L D P Q E L D I L K T V K E I T G F L L I Q A

W P E N R T D L H A F E N L E I I R G R T K Q H G

Q F S L A V V S L N I T S L G L R S L K E I S D G

D V I I S G N K N L C Y A N T I N W K K L F G T S

G Q K T K I I S N R G E N S C K A T G Q V C H A L

C S P E G C W G P E P R D C V S V E C P P C P A P

P V A G P S V F L F P P K P K D T L M I S R T P E

V T C V V V D V S H E D P E V Q F N W Y V D G M E

V H N A K T K P R E E Q F N S T F R V V S V L T V

V H Q D W L N G K E Y K C K V S N K G L P A P I E

K T I S K T K G Q P R E P Q V Y T L P P S R E E M

T K N Q V S L T C L V K G F Y P S D I A V E W E S

N G Q P E N N Y K T T P P M L D S D G S F F L Y S

K L T V D K S R W Q Q G N V F S C S V M H E A L H

N H Y T Q K S L S L S P G K Stop

EXAMPLE 17

The present example refers to a chimera containing a signal peptide (M E W S W V F L F F L S V T T G V H S) joined to the LI subdomain and the modules 1-7 of the SI subdomain of the ErbB4 receptor and the module 8 of the SI subdomain, the LII subdomain and module 1 of the SII subdomain of the ErbB1 receptor fused to IgG2Fc. The ErbB chimera has the following amino acid sequence:

SEQ. ID. NO. 17

M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T R T V C A E Q C D G R C Y G P Y V S D C C H

R E C A G G C S G P K D T D C F A C M N F N D S G

A C V T Q C P Q T F V Y N P T T F Q L E H N F N A

K Y T Y G A F C V K K C P H N F V V D S S S C V R

A C P S S K M E V E E N G I K M C K P C E G P C R

K V C N G I G I G E F K D S L S I N A T N I K H F

K N C T S I S G D L H I L P V A F R G D S F T H T

-continued

P P L D P Q E L D I L K T V K E I T G F L L I Q A

W P E N R T D L H A F E N L E I I R G R T K Q H G

Q F S L A V V S L N I T S L G L R S L K E I S D G

D V I I S G N K N L C Y A N T I N W K K L F G T S

G Q K T K I I S N R G E N S C K A T G Q V C H A L

C S P E G C W G P E P R D C V S V E C P P C P A P

P V A G P S V F L F P P K P K D T L M I S R T P E

V T C V V V D V S H E D P E V Q F N W Y V D G M E

V H N A K T K P R E E Q F N S T F R V V S V L T V

V H Q D W L N G K E Y K C K V S N K G L P A P I E

K T I S K T K G Q P R E P Q V Y T L P P S R E E M

T K N Q V S L T C L V K G F Y P S D I A V E W E S

N G Q P E N N Y K T T P P M L D S D G S F F L Y S

K L T V D K S R W Q Q G N V F S C S V M H E A L H

N H Y T Q K S L S L S P G K Stop

EXAMPLE 18

The present example discloses a chimera containing a signal peptide (M E W S W V F L F F L S V T T G V H S) joined to the LI subdomain and module 1 of the SI subdomain of the ErbB4 receptor and modules 2-8 of the SI subdomain, the LII subdomain and module 1 of the SII subdomain of the ErbB1 receptor fused to IgG2Fc. The chimera has the following amino acid sequence:

SEQ. ID. NO. 18

M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T K I I C A Q Q C S G R C R G K S P S D C C H

N Q C A A G C T G P R E S D C L V C R K F R D E A

T C K D T C P P L M L Y N P T T Y Q M D V N P E G

K Y S F G A T C V K K C P R N Y V V T D H G S C V

R A C G A D S Y E M E E D G V R K C K K C E G P C

R K V C N G I G I G E F K D S L S I N A T N I K H

F K N C T S I S G D L H I L P V A F R G D S F T H

T P P L D P Q E L D I L K T V K E I T G F L L I Q

A W P E N R T D L H A F E N L E I I R G R T K Q H

G Q F S L A V V S L N I T S L G L R S L K E I S D

G D V I I S G N K N L C Y A N T I N W K K L F G T

S G Q K T K I I S N R G E N S C K A T G Q V C H A

L C S P E G C W G P E P R D C V S V E C P P C P A

P P V A G P S V F L F P P K P K D T L M I S R T P

E V T C V V V D V S H E D P E V Q F N W Y V D G M

E V H N A K T K P R E E Q F N S T F R V V S V L T

V V H Q D W L N G K E Y K C K V S N K G L P A P I

E K T I S K T K G Q P R E P Q V Y T L P P S R E E

M T K N Q V S L T C L V K G F Y P S D I A V E W E

S N G Q P E N N Y K T T P P M L D S D G S F F L Y

S K L T V D K S R W Q Q G N V F S C S V M H E A L

H N H Y T Q K S L S L S P G K Stop

EXAMPLE 19

The present example discloses a chimera containing a signal peptide (M E W S W V F L F F L S V T T G V H S) joined to the LI subdomain and modules 1-5 of the SI subdomain of the ErbB4 receptor (through amino acid residue 245 of the ErbB4 receptor in the alignment of FIG. 3) and modules 5-8 of the SI subdomain of the ErbB1 receptor (starting at amino acid residue 249 of the ErbB1 receptor in the alignment of FIG. 3), the LII subdomain and module 1 of the SII subdomain of the ErbB1 receptor, fused to IgG2Fc after amino acid 501 in the SII subdomain. Amino acid 245 is based on numbering of the ErbB4 receptor while amino acids 249 and 501 are based on numbering of the ErbB1 receptor. The chimera has the following amino acid sequence:

SEQ. ID. NO. 19
M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T R T V C A E Q C D G R C Y G P Y V S D C C H

R E C A G G C S G P K D T D C F A C M N F N D S G

A C V T Q C P Q T F V Y N P T T Y Q M D V N P E G

K Y S F G A T C V K K C P R N Y V V T D H G S C V

R A C G A D S Y E M E E D G V R K C K K C E G P C

R K V C N G I G I G E F K D S L S I N A T N I K H

F K N C T S I S G D L H I L P V A F R G D S F T H

T P P L D P Q E L D I L K T V K E I T G F L L I Q

A W P E N R T D L H A F E N L E I I R G R T K Q H

G Q F S L A V V S L N I T S L G L R S L K E I S D

G D V I I S G N K N L C Y A N T I N W K K L F G T

S G Q K T K I I S N R G E N S C K A T G Q V C H A

L C S P E G C W G P E P R D C V S V E C P P C P A

P P V A G P S V F L F P P K P K D T L M I S R T P

E V T C V V V D V S H E D P E V Q F N W Y V D G M

E V H N A K T K P R E E Q F N S T F R V V S V L T

V V H Q D W L N G K E Y K C K V S N K G L P A P I

E K T I S K T K G Q P R E P Q V Y T L P P S R E E

M T K N Q V S L T C L V K G F Y P S D I A V E W E

S N G Q P E N N Y K T T P P M L D S D G S F F L Y

S K L T V D K S R W Q Q G N V F S C S V M H E A L

H N H Y T Q K S L S L S P G K Stop

EXAMPLE 20

The present example discloses a chimera containing the LI subdomain and modules 1-5 of the SI subdomain of the ErbB4 receptor (through amino acid residue 245 of the ErbB4 receptor in the alignment of FIG. 3) and modules 5-8 of the SI subdomain of the ErbB1 receptor (starting at amino acid residue 249 of the ErbB1 receptor in the alignment of FIG. 3), the LII subdomain and module 1 of the SII subdomain of the ErbB1 receptor, fused to IgG2Fc after amino acid 501 in the SII subdomain. Amino acid 245 is based on numbering of the ErbB4 receptor while amino acids 249 and 501 are based on numbering of the ErbB1 receptor. Additionally, this sequence contains 2 cysteine (Cys) to serine (Ser) substitutions in the hinge region of IgG2Fc. These substitutions are C226S and C229S, based on numbering of the IgG2Fc protein and are underlined below. The chimera has the following amino acid sequence:

SEQ. ID. NO. 20
M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T R T V C A E Q C D G R C Y G P Y V S D C C H

R E C A G G C S G P K D T D C F A C M N F N D S G

A C V T Q C P Q T F V Y N P T T Y Q M D V N P E G

K Y S F G A T C V K K C P R N Y V V T D H G S C V

R A C G A D S Y E M E E D G V R K C K K C E G P C

-continued

```
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E S P P S P A
P P V A G P S V F L P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop
```

EXAMPLE 21

This example demonstrates that ErbB chimeras having substantial binding affinity for ligands to both receptors can be created from the selective combination of two different ErbB receptors. Four constructs were tested for binding to HRG1β and TGFα including the construct from Example 19 (Seq ID No. 19), designated for purposes of this example as E1/E4-Fc, and the construct from Example 20 (Seq ID No. 20) which is designated E1/E4-MFc. The controls included amino acids 1-501 of ErbB1 joined to the IgG2Fc portion, designated E1 and amino acids 1-497 of ErbB4 joined to the IgG2Fc portion, designated E4. In some studies another E1 control was used.

Trap DNA molecules were synthesized by starting with the desired amino acid sequence and optimizing the DNA sequence for mammalian system expression. Trap DNA sequences were cloned into a suitable mammalian expression vector (pCpGfree-vitroHmcs) that can be selected using hygromycin and contains MAR/SAR sequences (insulator and boundary regions) and promoters and enhancers for trap expression. Vectors containing trap sequences were transfected into CHO cells by standard transfection methods and the cells were selected for vector integration with hygromycin. Traps were purified from stably transfected cell lines by collecting cell culture medium and purifying by standard methods (protein A column binding). Traps were eluted from protein A by standard methods and quantitated using a custom derived IgG-Fc sandwich ELISA assay.

Traps were purified using protein A and run on a polyacrylamide gel, under non-reducing (NR) and reducing (R) conditions. Disulfide linked dimers run at approximately 220-240 kDa, while reduced monomers run at 120-130 kDa. The chimeric trap monomer with mutated cysteines that prevent disulfide formation runs at approximately 120-130 kDa under both non-reducing and reducing conditions. The E1-Fc, E4-Fc, E1/E4-Fc appeared to be in the 220-240 kDa range when run under nonreducing conditions and in the range of about 120-130 when run under reducing conditions. The E1/E4-Fc construct appeared to have molecular weight of about 120-130 under both nonreducing and reducing conditions.

Purified trap molecules were coated on 96 well plates and incubated with either TGFα or HRG1β. Then detection antibodies against TGFα or HRG1β were used to measure the affinity (Kd) and amount of bound ligand (Bmax).

Traps were coated on 96 well plates and incubated with varying concentrations of either TGFα or HRG1β. Detection antibodies against TGFα or HRG1β were used to measure the affinity (Kd) and amount of bound ligand (Bmax). Data obtained in these studies is provided in Tables 1-4 below.

As set forth in Tables 1 and 2, the chimeric monomer (E1/E4-Fc) bound TGFα with an affinity in the range of about 400-620 nM and ErbB1-IgGFc (E1-Fc) bound with an affinity (Kd) in the range of about 27-40 nM.

TABLE 1

| | TGFα Binding Study | | | | |
|---|---|---|---|---|---|
| | E1-Fc | E4-Fc | E1/E4-Fc | E1/E4-MFc | E1-control |
| Bmax | 970,300 | 1,249,000 | 2,410,000 | 2,509,000 | 1,118,000 |
| Kd (nM) | 27.48 | 4.895 | 676.7 | 406.5 | 18.47 |
| Std Error Bmax | 101,600 | 24,510 | 478,600 | 392,300 | 73,470 |
| Std Error Kd (nM) | 12.69 | 5.887 | 266.2 | 149 | 5.72 |

TABLE 2

| | TGFα Binding Study | | | | |
|---|---|---|---|---|---|
| | E1-Fc | E4-Fc | E1/E4-Fc | E1/E4-MFc | E1/E4M-50% |
| Bmax | 781,267 | 280,121 | 834,302 | 695,464 | 779,310 |
| Kd (nM) | 40.33 | 10601 | 344.8 | 621.2 | 1953 |
| Std Error Bmax | 45,287 | 2,180,000 | 113,865 | 137,557 | 338,644 |
| Std Error Kd (nM) | 9.847 | 89561 | 116.3 | 250.5 | 1208 |

As shown in Tables 3 and 4, the chimeric monomer (E1/E4-Fc) bound HRG1β with an affinity in the range of about approximately 15-30 nM which was essentially the same as ErbB4-IgGFc (E4-Fc).

TABLE 3

HRG1β Binding Study

|  | E1/E4-Fc BATCH1 | E1/E4-Fc BATCH 2 | E1/E4-MFc | E4-Fc |
|---|---|---|---|---|
| Bmax | 1,460,000 | 1,630,000 | 4,440,000 | 2,880,000 |
| Kd (nM) | 13.1 | 17.3 | 27.77 | 21.18 |
| Std Error Bmax | 38,008 | 56,194 | 176,175 | 120,882 |
| Std Error Kd (nM) | 1.255 | 2.055 | 3.375 | 2.92 |

TABLE 4

HRG1β Binding Study

|  | E1/E4-Fc | E1/E4-MFc | E1/E4-MFc 50% | E4-Fc |
|---|---|---|---|---|
| Bmax | 1,900,000 | 6,360,000 | 3,110,000 | 1,480,000 |
| Kd (nM) | 23.82 | 26.62 | 15.46 | 14.51 |
| Std Error Bmax | 135,806 | 876,498 | 179,457 | 117,757 |
| Std Error Kd (nM) | 3.932 | 8.175 | 2.366 | 3.128 |

The E1/E4-MFc 50% data point shows that when one half of the amount of the purified chimeric receptor is added to a well that binding goes down by half and therefore binding is proportional to the amount of added receptor.

This example demonstrates that ErbB chimeras can be created and purified that have substantial affinity for ligands to both of its receptor subcomponents. Further this example shows that mutations can be introduced into the chimeric receptor binding molecules to change disulfides to prevent the formation of dimers through disulfide bond formation.

EXAMPLE 22

The present example discloses a chimera containing a signal peptide (M E W S W V F L F F L S V T T G V H S) joined to amino acids 1-245 of the ErbB4 receptor and amino acids 249 to 501 of the ErbB1 receptor. The fusion also includes IgG2-Fc as in the sequences above. Also incorporated into this sequence is a substitution of glutamine for serine at position 13 and the two cysteine to serine modifications from example 20 that prevent disulfide based dimerization of the molecule. The glutamine at position 13 (underlined below) is found in the ErbB1 sequence at that location and is incorporated in the sequence to increase the affinity of the chimera for TGFα. The ErbB chimera has the following amino acid sequence:

```
                                        SEQ. ID. NO. 21
M E W S W V F L F F L S V T T G V H S Q S V C A G
T E N K L S Q L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C H K S C T G R C W G P T E N H C Q
                    -continued
T L T R T V C A E Q C D G R C Y G P Y V S D C C H
R E C A G G C S G P K D T D C F A C M N F N D S G
A C V T Q C P Q T F V Y N P T T Y Q M D V N P E G
K Y S F G A T C V K K C P R N Y V V T D H G S C V
R A C G A D S Y E M E E D G V R K C K K C E G P C
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E S P P S P A
P P V A G P S V F L F P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop
```

EXAMPLE 23

The present example discloses a chimera containing a signal peptide (M E W S W V F L F F L S V T T G V H S) joined to amino acids 1-245 of the ErbB4 receptor and amino acids 249 to 501 of the ErbB1 receptor. The fusion also includes IgG2-Fc as in the sequences above. Also incorporated into this sequence is a substitution of tyrosine for serine at position 42 and the two cysteine to serine modifications from example 20 that prevent disulfide based dimerization of the molecule. The tyrosine (underlined below) at position 42 is found in the ErbB1 sequence at that location and is incorporated in the sequence to increase the affinity of the chimera for TGFα. The ErbB chimera has the following amino acid sequence:

SEQ. ID. NO. 22
M E W S W V F L F F L S V T T G V H S Q S V C A G
T E N K L S S L S D L E Q Q Y R A L R K Y Y E N C
E V V M G N L E I T Y I E H N R D L S F L R S V R
E V T G Y V L V A L N Q F R Y L P L E N L R I I R
G T K L Y E D R Y A L A I F L N Y R K D G N F G L
Q E L G L K N L T E I L N G G V Y V D Q N K F L C
Y A D T I H W Q D I V R N P W P S N L T L V S T N
G S S G C G R C H K S C T G R C W G P T E N H C Q
T L T R T V C A E Q C D G R C Y G P Y V S D C C H
R E C A G G C S G P K D T D C F A C M N F N D S G
A C V T Q C P Q T F V Y N P T T Y Q M D V N P E G
K Y S F G A T C V K K C P R N Y V V T D H G S C V
R A C G A D S Y E M E E D G V R K C K K C E G P C
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E S P P S P A
P P V A G P S V F L F P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop

EXAMPLE 24

The present example discloses a chimera containing a signal peptide (M E W S W V F L F F L S V T T G V H S) joined to amino acids 1-245 of the'ErbB4 receptor and amino acids 249 to 501 of the ErbB1 receptor. The fusion also includes IgG2-Fc as in the sequences above. Also incorporated into this sequence is a substitution of arginine for tyrosine at position 123 (underlined) and the two cysteine to serine modifications from example 20 that prevent disulfide based dimerization of the molecule. The arginine at position 123 is found in the ErbB1 sequence at that location and is incorporated in the sequence to increase the affinity of the chimera for TGFα. The ErbB chimera has the following amino acid sequence:

SEQ. ID. NO. 23
M E W S W V F L F F L S V T T G V H S Q S V C A G
T E N K L S S L S D L E Q Q Y R A L R K Y Y E N C
E V V M G N L E I T S I E H N R D L S F L R S V R
E V T G Y V L V A L N Q F R Y L P L E N L R I I R
G T K L Y E D R Y A L A I F L N V R K D G N F G L
Q E L G L K N L T E I L N G G V R V D Q N K F L C
Y A D T I H W Q D I V R N P W P S N L T L V S T N
G S S G C G R C H K S C T G R C W G P T E N H C Q
T L T R T V C A E Q C D G R C Y G P Y V S D C C H
R E C A G G C S G P K D T D C F A C M N F N D S G
A C V T Q C P Q T F V Y N P T T Y Q M D V N P E G
K Y S F G A T C V K K C P R N Y V V T D H G S C V
R A C G A D S Y E M E E D G V R K C K K C E G P C
R K V C N G I G I G E F K D S L S I N A T N I K H
F K N C T S I S G D L H I L P V A F R G D S F T H
T P P L D P Q E L D I L K T V K E I T G F L L I Q
A W P E N R T D L H A F E N L E I I R G R T K Q H
G Q F S L A V V S L N I T S L G L R S L K E I S D
G D V I I S G N K N L C Y A N T I N W K K L F G T
S G Q K T K I I S N R G E N S C K A T G Q V C H A
L C S P E G C W G P E P R D C V S V E S P P S P A
P P V A G P S V F L F P P K P K D T L M I S R T P
E V T C V V V D V S H E D P E V Q F N W Y V D G M
E V H N A K T K P R E E Q F N S T F R V V S V L T
V V H Q D W L N G K E Y K C K V S N K G L P A P I
E K T I S K T K G Q P R E P Q V Y T L P P S R E E
M T K N Q V S L T C L V K G F Y P S D I A V E W E
S N G Q P E N N Y K T T P P M L D S D G S F F L Y
S K L T V D K S R W Q Q G N V F S C S V M H E A L
H N H Y T Q K S L S L S P G K Stop

EXAMPLE 25

The present example discloses a chimera containing a signal peptide (M E W S W V F L F F L S V T T G V H S) joined to amino acids 1-183 of the ErbB4 receptor and amino acids 187-501 of the ErbB1 receptor. The sequence is essentially the same as the sequence in Example 18, except that it contains two cysteine to serine modifications in the IgG2Fc region to prevent dimerization (as in example 20). This fusion contains more ErbB1 sequence in order to increase the binding affinity of the chimera for TGFα. The ErbB chimera has the following amino acid sequence:

SEQ. ID. NO. 24

M E W S W V F L F F L S V T T G V H S Q S V C A G

T E N K L S S L S D L E Q Q Y R A L R K Y Y E N C

E V V M G N L E I T S I E H N R D L S F L R S V R

E V T G Y V L V A L N Q F R Y L P L E N L R I I R

G T K L Y E D R Y A L A I F L N Y R K D G N F G L

Q E L G L K N L T E I L N G G V Y V D Q N K F L C

Y A D T I H W Q D I V R N P W P S N L T L V S T N

G S S G C G R C H K S C T G R C W G P T E N H C Q

T L T K I I C A Q Q C S G R C R G K S P S D C C H

N Q C A A G C T G P R E S D C L V C R K F R D E A

T C K D T C P P L M L Y N P T T Y Q M D V N P E G

K Y S F G A T C V K K C P R N Y V V T D H G S C V

R A C G A D S Y E M E E D G V R K C K K C E G P C

-continued

R K V C N G I G I G E F K D S L S I N A T N I K H

F K N C T S I S G D L H I L P V A F R G D S F T H

T P P L D P Q E L D I L K T V K E I T G F L L I Q

A W P E N R T D L H A F E N L E I I R G R T K Q H

G Q F S L A V V S L N I T S L G L R S L K E I S D

G D V I I S G N K N L C Y A N T I N W K K L F G T

S G Q K T K I I S N R G E N S C K A T G Q V C H A

L C S P E G C W G P E P R D C V S V E S P P S P A

P P V A G P S V F L F P P K P K D T L M I S R T P

E V T C V V V D V S H E D P E V Q F N W Y V D G M

E V H N A K T K P R E E Q F N S T F R V V S V L T

V V H Q D W L N G K E Y K C K V S N K G L P A P I

E K T I S K T K G Q P R E P Q V Y T L P P S R E E

M T K N Q V S L T C L V K G F Y P S D I A V E W E

S N G Q P E N N Y K T T P P M L D S D G S F F L Y

S K L T V D K S R W Q Q G N V F S C S V M H E A L

H N H Y T Q K S L S L S P G K Stop

The invention claimed is:

1. A chimeric ErbB ligand binding molecule monomer comprising an amino acid sequence selected from the group of amino acid sequences consisting of SEQ ID NOS: 14, 15, and 20.

2. The chimeric ErbB ligand binding molecule monomer of claim 1 further comprising, an immunoglobulin Fc portion.

3. A dimer comprising two chimeric ErbB ligand binding molecule monomers of claim 2.

* * * * *